US008523763B2

(12) United States Patent
Sinai et al.

(10) Patent No.: US 8,523,763 B2
(45) Date of Patent: Sep. 3, 2013

(54) LUMEN PROBE APPARATUSES AND METHODS FOR USING THE SAME

(75) Inventors: Nir Sinai, Alon HaGalil-Doar-Na HaMovil (IL); Idan Boader, Carmiel (IL)

(73) Assignee: Inmotion Medical Ltd., Katzrin (IL)

( * ) Notice: Subject to any disclaimer, the term of this patent is extended or adjusted under 35 U.S.C. 154(b) by 466 days.

(21) Appl. No.: 12/738,077

(22) PCT Filed: Oct. 16, 2008

(86) PCT No.: PCT/IB2008/054255
§ 371 (c)(1),
(2), (4) Date: Apr. 15, 2010

(87) PCT Pub. No.: WO2009/050668
PCT Pub. Date: Apr. 23, 2009

(65) Prior Publication Data
US 2010/0240955 A1    Sep. 23, 2010

Related U.S. Application Data

(60) Provisional application No. 60/960,828, filed on Oct. 16, 2007.

(51) Int. Cl.
*A61B 1/00* (2006.01)
(52) U.S. Cl.
USPC .................................................. 600/116
(58) Field of Classification Search
USPC ............................................ 600/115, 116
See application file for complete search history.

(56) References Cited

U.S. PATENT DOCUMENTS

| 4,315,512 | A | | 2/1982 | Fogarty |
| 4,690,131 | A | | 9/1987 | Lyddy, Jr. et al. |
| 4,838,859 | A | | 6/1989 | Strassmann |
| 4,976,689 | A | | 12/1990 | Buchbinder et al. |
| 5,398,670 | A | | 3/1995 | Ortiz et al. |
| 5,662,587 | A | * | 9/1997 | Grundfest et al. ............ 600/114 |
| 5,728,123 | A | | 3/1998 | Lemelson et al. |
| 6,007,482 | A | * | 12/1999 | Madni et al. .................. 600/115 |
| 6,764,441 | B2 | | 7/2004 | Chiel et al. |
| 7,022,068 | B2 | * | 4/2006 | Kim et al. .................... 600/115 |

(Continued)

FOREIGN PATENT DOCUMENTS

| JP | 08-089476 | 4/1996 |
| JP | 10-127564 | 5/1998 |

(Continued)

OTHER PUBLICATIONS

Communication Pursuant to Article 94(3) EPC Dated Nov. 9, 2011 From the European Patent Office Re. Application No. 08807975.1.

(Continued)

*Primary Examiner* — W B Perkey

(57) ABSTRACT

A probe apparatus adapted for movement through a lumen, comprising: a linearly extendible and retractable element adapted for selective extension and retraction to provide the movement; a front balloon positioned forward of the linearly extendible and retractable element and adapted for selective inflation and deflation; a rear balloon positioned backward of the linearly extendible and retractable element and adapted for selective inflation and deflation; and, a twisting element adapted to twist at least one of the linearly extendible and retractable element, front balloon and rear balloon during inflation and deflation of the advancement balloon.

19 Claims, 17 Drawing Sheets

(56) References Cited

U.S. PATENT DOCUMENTS

2002/0052638 A1    5/2002  Zadno-Azizi
2003/0060680 A1    3/2003  Wendlandt
2004/0102681 A1*   5/2004  Gross .......................... 600/116

FOREIGN PATENT DOCUMENTS

| JP | 2006-026343 | 2/2006 |
| WO | WO 00/44275 | 8/2000 |
| WO | WO 2009/050668 | 4/2009 |

OTHER PUBLICATIONS

Communication Pursuant to Article 94(3) EPC Dated Jun. 8, 2012 From the European Patent Office Re. Application No. 08807975.1.
Phee et al. "Locomotion and Steering Aspects in Automation of Colonoscopy. Part One: A Literature Review", IEEE Engineering in Medicine and Biology, p. 85-96, Nov./Dec. 1997.
Response Dated Aug. 14, 2011 to Supplementary European Search Report and the European Search Opinion Dated Jan. 26, 2011 From the European Patent Office Re. Application No. 08807975.1.
Office Action Dated Aug. 25, 2011 From the Israeli Patent Office Re. Application No. 205147.
Written Opinion Dated Mar. 2, 2009 From the International Searching Authority Re.: Application No. PCT/IB2008/054255.
Supplementary European Search Report and the Written Opinion Dated Jan. 26, 2011 From the European Patent Office Re. Application No. 08807975.1.
International Preliminary Report on Patentability Dated Jan. 27, 2010 From the International Preliminary Examining Authority Re.: Application No. PCT/IB08/54255.
International Search Report Dated Mar. 2, 2009 From the International Searching Authority Re.: Application No. PCT/IB2008/054255.
International Preliminary Report on Patentability Dated pr. 29, 2010 From the International Bureau of WIPO Re.: Application No. PCT/IB2008/054255.
Translation of Notice of Reason for Rejection Dated Dec. 7, 2012 From the Japanese Patent Office Re. Application No. 2010-529486.
Communication Pursuant to Article 94(3) EPC Dated Feb. 5, 2013 From the European Patent Office Re. Application No. 08807975.1.

* cited by examiner

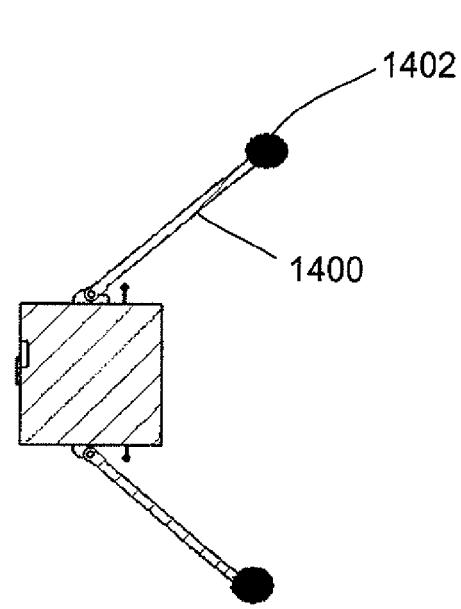
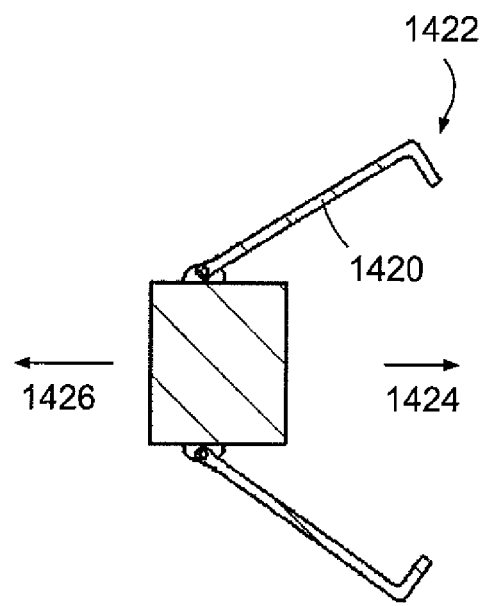
FIG. 14A                FIG. 14B
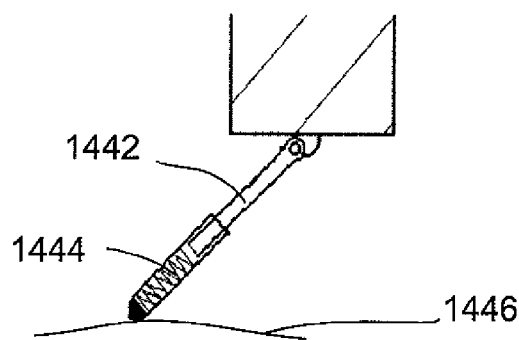
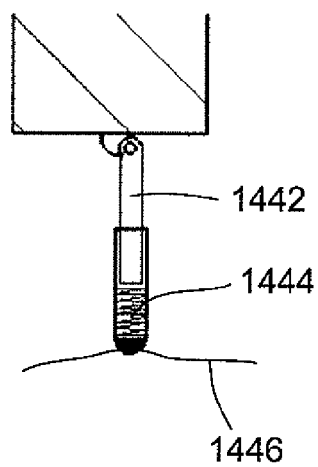
FIG. 14C                FIG. 14D

US 8,523,763 B2

LUMEN PROBE APPARATUSES AND METHODS FOR USING THE SAME

RELATED APPLICATIONS

This application is a National Phase Application of PCT patent application Ser. No. PCT/IB2008/054255 having International Filing Date of Oct. 16, 2008, which claims the benefit under 35 U.S.C. §119(e) of U.S. Provisional Patent Application No. 60/960,828, filed on Oct. 16, 2007. The contents of the above Applications are incorporated herein by reference.

FIELD AND BACKGROUND OF THE INVENTION

The present invention, in some embodiments thereof, relates to apparatuses for probing lumens and, more particularly, but not exclusively, to a probe apparatus adapted to twist and/or travel in a plurality of directions.

Probes for use within body lumens include endoscopes used in endoscopy procedures. Endoscopy is a minimally invasive medical procedure that is used to assess the interior surfaces of an organ by inserting a tube into the body. The instrument may have a rigid or flexible tube and not only provide an image for visual inspection and photography, but also enable taking biopsies and retrieval of foreign objects. A specific example of an endoscopic procedure is a colonoscopy.

Many endoscopic procedures are considered to be relatively painless and, at worst, associated with mild discomfort. Complications are not common (only 5% of all operations) but can include perforation of the organ under inspection with the endoscope or biopsy instrument. If that occurs, open surgery may be required to repair the injury.

U.S. Pat. No. 4,066,070 describes main and auxiliary cuffs made of an elastic material such as rubber, etc., are mounted in close proximity to each other on the forward end portion of a flexible sheath of a tubular medical instrument. The flexible sheath is inserted into a body cavity of a human being and with further insertion of the flexible tube the main cuff is contacted, while at the expanded state, with the wall surface of the body cavity and when the flexible sheath is forwardly pushed the portion of the main cuff is rearwardly deformed, while effecting a rolling contact with the wall surface of the body cavity, to permit it to ride on the auxiliary cuff. When the auxiliary cuff is then expanded to cause the corresponding wall surface of the body cavity to be expanded, the main cuff is separated away from the wall surface of the body cavity to cause the portion of the main cuff to be forwardly pushed ahead into an original position. Such a step is cyclically repeated so that the sheath can be intermittently advanced into the body cavity of the human being.

U.S. Pat. No. 4,676,228 describes a medical device for use with an elongated flexible instrument of the type adapted to at least partially extend into the lumen of a tubular body part and having a front end for leading said instrument through said lumen and a rear end opposite said front end. The device comprises (a) an elongated flexible sheath capable of being coaxially mounted on and axially slidable with respect to said instrument between said front and rear ends of said instrument and (b) an integrally-formed cuff assembly including a front inflatable cuff section adapted to be secured to the front end of said instrument, a rear inflatable cuff section adapted to be secured to the front end of said sheath and a middle expandable section integrally formed with said front and rear cuff sections for protecting that portion of said instrument between the position of said front and rear cuffs.

U.S. Pat. No. 4,690,131 describes an improved device of a combination of elements is adapted to be used with an elongated flexible instrument, such as an endoscope, and capable of at least partially extending with the instrument into the lumen of a tubular body part, such as the large intestines. A sheath is adapted to be mounted on the instrument. The instrument and sheath are provided with selectively inflatable cuffs movable with respect to one another by axially sliding the sheath on the instrument. The movable relationship of the sheath and instrument and the selective control of air to the cuffs allows the user to more easily navigate the front of the instrument through the lumen of the body part with less discomfort to the patient.

U.S. Pat. No. 5,144,848 describes an intra-tube traveling apparatus includes a moving unit to which an endoscope is held and which is self-driven to travel in a pipe path, and a movement control section for controlling movement of the moving unit. The moving unit includes an elastic actuator which is extended/contracted in the radial direction and axial directions of the pipe path upon reception of the pressurized fluid, balloons attached to the front and rear ends of the elastic actuator. Each of the balloons is radially expanded/deformed upon reception of the pressurized fluid therein to be locked to the inner surface of the pipe path. The movement control section includes a pressurized fluid supply unit, a switching control section, a stop signal output switch for outputting a stop signal for stopping a movement operation of the moving unit, and a unit fixing portion for supplying the pressurized fluid to the balloons upon reception of the stop signal from the stop signal output switch to expand/deform the lock portions, thereby fixing the moving unit to the inner surface of the pipe path.

U.S. Pat. No. 5,454,364 describes a medical instrument, particularly an endoscope, is provided with a device to guide the instrument within the intestine. The device is forwardly movable stepwise within the intestine with intermittent contact with the intestine wall. The device is so constructed to enable one to first push together on the instrument a part of the intestine surrounding the instrument, and then the device can be quickly pushed forward by taking advantage of the intestine's own inertia U.S. Pat. No. 5,906,591 describes an endoscopic robot designed for being inserted into a body cavity of a patient and advanced therein in a prefixed direction with a so-called inchworm-like motion, comprising a variable length segment and aspiration means for selectively producing a pneumatic vacuum between the robot and the body cavity at the robot ends sufficient to produce a substantial anchorage to the body cavity walls, thereby allowing the inchworm-like motion and avoiding, at the same time, any pushing action against the body cavity walls which causes discomfort and pain to the patient.

U.S. Pat. No. 6,007,482 describes an endoscope which is both flexible and easily cleaned having a pair of extending sections at its distal end one of which carries a camera and which are alternately actuated to provide movement through a body passageway by a Bowden type of cable. Such cable has an outer helical casing with an inner steel wire. Respectively attached to the two cylindrical sections are inflatable bladders which provide for the movement above which also are an integral part of the flexible sterilized sheath being held to the respective sections by O-rings.

U.S. App. Pub. No. 2004073082 describes an endoscopic device for locomotion in a body cavity according to a prefixed advancing direction comprising at least a variable length intermediate section extending between a front end section and a rear end section. First and second clamping means are integral to the front and rear section, for alternately grasping respective surrounding portions of wall of the body cavity. Sucking means are associated to the first and second clamping means for creating a depression sufficient to cause the body cavity wall portions to collapse within the first and second clamping means while they are in an open condition. Means for actuating alternate extensions and retractions of the intermediate section and actuating means of the first and second clamping means are further provides for synchronous operation to generate a forward motion of the rear end section due to a retraction of the intermediate section, the wall portion surrounding the first clamping means being firmly held therebetween, and to generate a forward motion of the front end section due to an extension of the intermediate section, the wall portion surrounding the second clamping means being firmly held therebetween.

SUMMARY OF THE INVENTION

An aspect of some embodiments of the invention relates to providing balloon type probe apparatuses for navigating forward (moving further into a lumen) and/or backward (moving towards an insertion point and/or out of the lumen) in a lumen while twisting. Optionally, the twisting reduces trauma to the lumen. Optionally, twisting maintains probe apparatus position with respect to lumen during movement (e.g. keeps the probe centered). In an embodiment of the invention, selective inflation and/or deflation of at least one balloon causes forward and/or backward movement of the probe apparatus in a lumen. In an embodiment of the invention, the lumen is a body lumen, for example a colon or an artery or vein. In some embodiments of the invention, the lumen is in an inanimate object, for example a sewer pipe or a conduit.

In an embodiment of the invention, the probe apparatus is comprised of at least one of a front balloon section, an advancement balloon section and/or a rear balloon section.

In an embodiment of the invention, twisting is provided to probe apparatus during inflation and/or deflation of a linearly extending and/or retracting object, such as an advancement balloon. In an embodiment of the invention, the probe apparatus is adapted to twist using a spring. In some embodiments of the invention, the twisting is provided by at least one elastic band.

Probe apparatus is optionally adapted to accommodate at least one medical instrument, for example an endoscope. In an embodiment of the invention, the at least one medical instrument is inserted into the probe apparatus through an instrument channel which extends the length of the apparatus. In some embodiments of the invention, the instrument channel twists independently of other elements of the probe apparatus in order to provide stability for the medical instruments.

In some embodiments of the invention, the probe apparatus is adapted for providing a stable platform from which the at least one medical instrument can operate since at least one of the front balloon section and the rear balloon section can anchor the probe apparatus in the lumen, thus any medical instrument in the probe apparatus is also anchored with respect to the lumen, in an embodiment of the invention. Optionally, the medical instrument is not anchored with respect to the lumen even though the probe apparatus is.

In some embodiments of the invention, at least one supply line is provided to the probe apparatus to supply as examples, inflation material and/or power. Optionally, inflation material is air. Optionally, inflation material is a fluid.

In an embodiment of the invention, the advancement balloon is provided with a sealing sleeve along the balloon's inner circumference in order to trap inflation material between the external surface of the advancement balloon and the sealing sleeve, leaving a void in the center of the probe apparatus.

In an embodiment of the invention, the probe apparatus is provided with a sliding gasket for preventing leakage of inflation material from out of the center of the probe apparatus while still allowing the instrument channel and/or a supply line within the instrument channel to slide relative to the gasket. In some embodiments of the invention, the sliding gasket is used when the probe apparatus is not adapted with a sealing sleeve.

In an exemplary embodiment of the invention, at least one balloon of the probe apparatus has an exterior surface which is adapted to interface with an inner circumference of the lumen, in an embodiment of the invention. For example, the exterior surface is provided with surface features which act as counterparts to surface features of the lumen.

In some embodiments of the invention, a plurality of separately inflatable and/or deflatable balloons is used at least one of the front or rear balloon sections to provide deflection of a tip of the probe apparatus with respect to the lumen. In an embodiment of the invention, the tip is jointed.

An aspect of some embodiments of the invention relates to providing arm type probe apparatuses for navigating forward and/or backward in a lumen while, in some embodiments of the invention, twisting to reduce trauma to the lumen. In some embodiments of the invention, the probe apparatus is provided with at least one arm element which biases movement of the apparatus either forward or backward. In an embodiment of the invention, arm element is a lever. In some embodiments of the invention, arm element is a leaf spring. Optionally, arm element is a coil which acts like a lever and/or a leaf spring. In an embodiment of the invention, motion bias from forward to backward and/or vice versa is effectuated by pulling and/or pushing on at least one supply line. In an embodiment of the invention, forward and/or backward motion is imparted to the probe apparatus using a linearly extendible and/or retractable element, such as an advancement balloon.

In some embodiments of the invention, at least one selectively inflatable and/or deflatable balloon is used to switch the bias of the at least one arm element from forward to backward and/or vice versa.

The at least one arm element has a tip adapted to reduce pressure on the lumen wall, for example by increasing the surface area of the tip using a ball-shaped contact object, in an exemplary embodiment of the invention.

The at least one arm element has a tip adapted to enhance the forward and/or backward bias of the at least one atm element and/or to allow movement simultaneously in a desired direction, in an exemplary embodiment of the invention. In an embodiment of the invention, the tip is v-shaped.

In some embodiments of the invention, the at least one arm element is adapted to reduce a dimension, for example by making the at least one arm element extendible. Optionally, the extending is controlled by a compression spring.

An aspect of some embodiments of the invention relates to providing a method of using a balloon type probe apparatus wherein selective inflation and/or deflation of at least one balloon causes movement and/or twisting of the probe apparatus. In an embodiment of the invention, at least one front balloon, advancement balloon and/or rear balloon is selectively inflated and/or deflated.

In some embodiments of the invention, a rear balloon is inflated substantially securing the probe in the lumen. An advancement balloon is inflated advancing a front balloon section of the apparatus forward in the lumen. The front balloon is inflated substantially securing the probe apparatus in the lumen, irrespective of the inflated rear balloon. The rear balloon and/or the advancement balloon are at least partially deflated, drawing the rear balloon closer to the front balloon. The rear balloon is inflated again, the front balloon is deflated and the cycle optionally begins again. In an embodiment of the invention, the cycle is reversed to advance the probe apparatus backwards in the lumen.

In some embodiments of the invention, at least one of the front balloon, advancement balloon and/or the rear balloon twists during inflation and/or deflation of the advancement balloon.

In an embodiment of the invention, at least one medical instrument is placed in the probe apparatus and navigated, using the probe apparatus, to a treatment site in the lumen.

An aspect of some embodiments of the invention relates to providing a method of navigating a curve in a lumen, including inflating an advancement balloon to move at least a part of a probe apparatus around the curve and then optionally deflating the advancement balloon to move at least another part of the probe apparatus around the curve to complete the navigating of the curve.

An aspect of some embodiments of the invention relates to providing a method of using an arm type probe apparatus provided with at least one arm element, including at least partially inflating an advancement balloon to move at least a first part of the probe apparatus and optionally deflating the advancement balloon to move at least a second part of the probe apparatus towards the first part. In an embodiment of the invention, movement is biased forward by the at least one arm element.

In an embodiment of the invention, the bias of the arm element is switched to impart backward movement to the probe apparatus. Optionally, at least one balloon is used to switch the bias. In some embodiments of the invention, bias is switched by pulling on a supply line.

There is thus provided in accordance with an exemplary embodiment of the invention a probe apparatus adapted for movement through a lumen, comprising: a linearly extendible and retractable element adapted for selective extension and retraction to provide the movement; a front balloon positioned forward of the linearly extendible and retractable element and adapted for selective inflation and deflation; a rear balloon positioned backward of the linearly extendible and retractable element and adapted for selective inflation and deflation; and, a twisting element adapted to twist at least one of the linearly extendible and retractable element, front balloon and rear balloon during inflation and deflation of the advancement balloon. Optionally, the linearly extendible and retractable element is a selectively inflatable and deflatable advancement balloon. Optionally, the linearly extendible and retractable element is a piston.

In some exemplary embodiments of the invention, the twisting device comprises a spring. In some exemplary embodiments of the invention, the twisting device comprises at least one elastic band.

In some exemplary embodiments of the invention, the probe apparatus is adapted with an instrument channel for accommodating the insertion of at least one medical instrument. Optionally, the instrument channel twists independently of the linearly extendible and retractable element, front balloon and rear balloon.

In an embodiment of the invention, the probe apparatus is provided with at least one supply line. Optionally, the supply line provides power to the probe apparatus. Optionally, the supply line provides inflation material to the probe apparatus.

In an exemplary embodiment of the invention, the probe apparatus further comprises a sealing sleeve for insulating contents of the advancement balloon from an interior of the probe apparatus.

In an exemplary embodiment of the invention, the probe apparatus further comprises a sliding gasket adapted to prevent inflation material from leaking out of probe apparatus.

In an exemplary embodiment of the invention, a surface of at least one of the front balloon, rear balloon and the advancement balloon is textured to interface with an inner circumference of the lumen.

In an exemplary embodiment of the invention, at least one of the front balloon and rear balloon is comprised of a plurality of independently inflatable and deflatable balloons.

In an exemplary embodiment of the invention, the probe apparatus further comprises a jointed tip. Optionally, the jointed tip is deflected by the inflation of at least one balloon.

There is further provided in accordance with an exemplary embodiment of the invention a probe apparatus tip, comprising: a joint affixed to a balloon section of a probe apparatus; a first plate attached to the joint opposite the balloon section, wherein pivoting of the joint causes deflection of the plate with respect to the balloon section; and, an inflatable and deflatable balloon located between the plate and the balloon section and adapted to cause pivoting of the joint. Optionally, the first plate is a selectively inflatable and deflatable balloon.

In an exemplary embodiment of the invention, the probe apparatus tip further comprises at least a second joint, second plate and second inflatable and deflatable balloon, wherein the second joint and the second inflatable and deflatable balloon are located between the first plate and the second plate.

There is further provided in accordance with an exemplary embodiment of the invention a probe apparatus adapted for movement through a lumen, comprising: a linearly extendible element adapted for selective extension and retraction to provide the movement; and, at least one arm element adapted to selectively bias the movement of the probe apparatus forward or backward. Optionally, the linearly extendible element is an advancement balloon.

In an exemplary embodiment of the invention, the probe apparatus further comprises a supply line which when pulled in a proximal direction switches the bias of the at least one arm element.

In an exemplary embodiment of the invention, the probe apparatus further comprises at least one selectively and independently inflatable and deflatable balloon which when at least partially inflated switches the bias of the at least one arm element from forward to backward.

In an exemplary embodiment of the invention, the at least one arm element has a tip with at least one of an enhanced surface area or soft material of construction for reducing pressure on the lumen. Optionally, the at least one arm element has a v-shaped tip.

In some embodiments of the invention, the at least one arm element is extendible. Optionally, the extending of the arm element is controlled by a compression spring.

There is further provided in accordance with an exemplary embodiment of the invention a method of using a balloon type probe apparatus, comprising: inserting the probe apparatus in a lumen; inflating a rear balloon of the probe apparatus, substantially securing the probe apparatus in place in the lumen; at least partially extending a linearly extendible and retractable element of the probe apparatus to move a front balloon of the probe apparatus forward in the lumen; inflating the front balloon, substantially securing the probe apparatus in place in the lumen without regard for the rear balloon securing; and, deflating, at least partially, the rear balloon and retracting the linearly extendible and retractable element drawing the rear balloon closer to the front balloon. In an exemplary embodiment of the invention, the method of using a balloon type probe apparatus further comprises twisting at least one of the rear balloon, linearly extendible and retractable element and front balloon during the at least partially extending of the linearly extendible and retractable element. Optionally, at least one of a supply line or an instrument channel of the probe apparatus does not twist relative to the lumen when at least one of the rear balloon, linearly extendible and retractable element and front balloon twists.

In an exemplary embodiment of the invention, the method of using a balloon type probe apparatus further comprises restarting the method at deflating the front balloon after re-inflating the rear balloon.

There is further provided in accordance with an exemplary embodiment of the invention a method of navigating a curve in a lumen, comprising: inserting the probe apparatus in a lumen; inflating a rear balloon of the probe apparatus, substantially securing the probe apparatus in place in the lumen; at least partially extending a linearly extendible and retractable element of the probe apparatus to move a front balloon of the probe apparatus forward and around the curve in the lumen; inflating the front balloon, substantially securing the probe apparatus in place in the lumen without regard for the rear balloon securing; and, deflating, at least partially, the rear balloon and retracting the linearly extendible and retractable element drawing the rear balloon closer to the front balloon and around the curve in the lumen.

There is further provided in accordance with an exemplary embodiment of the invention a method of using an arm type probe apparatus, comprising: inserting the probe apparatus in a lumen; at least partially extending a linearly extendible and retractable element of the probe apparatus to move a front of the probe apparatus forward in the lumen; retracting, at least partially, the linearly extendible and retractable element drawing the rear of the probe apparatus closer to the front of the apparatus; and, switching a bias at least one arm element attached to the probe apparatus to reverse direction of travel of the probe apparatus. Optionally, switching bias is performed using at least one inflatable balloon. Optionally, switching bias is performed by pulling in a proximal direction on a supply line.

In an exemplary embodiment of the invention, once switching is performed backward travel of the probe apparatus is achieved using the same actions as forward travel.

BRIEF DESCRIPTION OF THE DRAWINGS

Some embodiments of the invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 14A-D are side views of various arm configurations, in accordance with exemplary embodiments of the invention;

DESCRIPTION OF EMBODIMENTS OF THE INVENTION

Figure 1A:
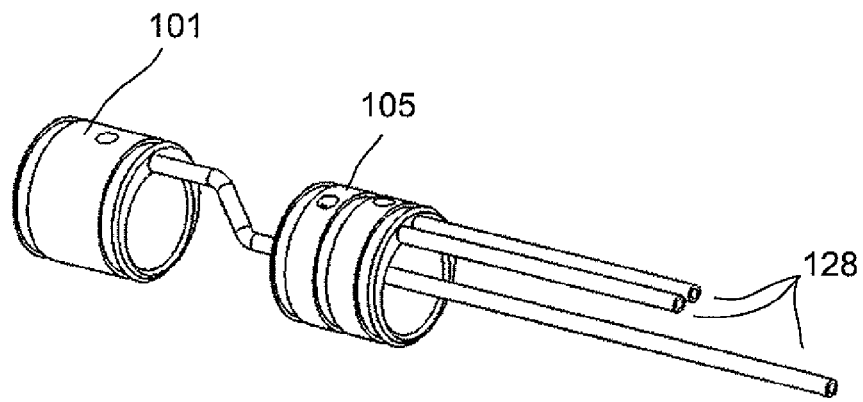
FIG. 1A is a perspective view of a front main body and a rear main body with a plurality of supply lines of a balloon type probe apparatus, in accordance with an exemplary embodiment of the invention.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways as will be apparent to those skilled in the relevant art.

Generally, described herein are apparatuses and methods for probing lumens and more particularly, but not exclusively, to probe apparatus embodiments. Probes such as those described herein, and variations thereof, are used for a wide variety of procedures involving body lumens and/or for non-biological purposes such as for examining and/or performing procedures on pipes internally and/or using the pipes and body lumens for transiting to where treatment and/or procedures are to be conducted. In some embodiments of the invention, exemplary probe apparatuses described herein are used to advance at least one medical instrument into and/or forward through the lumen to an area of interest and/or backwards out again. "Forward" as it is used herein indicates the direction of travel moving further into a lumen and away from an insertion point of an apparatus. "Backward" is therefore in a direction opposite forward, movement of an apparatus towards an insertion point and eventually, with sustained backward movement, out of the lumen.

In some embodiments of the invention, the probe apparatus is adapted for providing a stable platform from which the at least one medical instrument can operate since at least one of the front balloon section and the rear balloon section can anchor the probe apparatus in the lumen, thus any medical instrument in the probe apparatus is also anchored with respect to the lumen, in an embodiment of the invention. Optionally, the medical instrument is not anchored with respect to the lumen even though the probe apparatus is.

FIGS. 1A-1H depict various stages of assembly of a probe apparatus 100, in an exemplary embodiment of the invention. It should be noted that probe apparatus 100 is configured with a spring 102 and a linearly extendible and/or retractable element, such as an advancement balloon 104 including a sealing sleeve 106, described in more detail herein. Optionally, linearly extendible and/or retractable element is a piston, operated for example hydraulically. Incorporation of the sealing sleeve 106 with the advancement balloon 104 is optional. Additional embodiments are depicted in other Figures, including FIGS. 3A-5B. Probe apparatus 100 is comprised of three sections: a front balloon section 109, an advancement balloon section 103, and a rear balloon section 118, in an exemplary embodiment of the invention. Further details of probe apparatus 100 and the sections 109, 103 and 118 are described below.

Referring to FIG. 1A, a perspective view of a front main body 101 and a rear main body 105 with a plurality of supply lines 128 of a balloon type probe apparatus is shown, in accordance with an exemplary embodiment of the invention. In an embodiment of the invention, at least one of the front and/or rear main bodies 101, 105 is at least partially made from a plastic material. In some embodiments of the invention, at least one of the main bodies 101, 105 are at least partially constructed of metal. Optionally, the material is biocompatible.

Figure 1B:
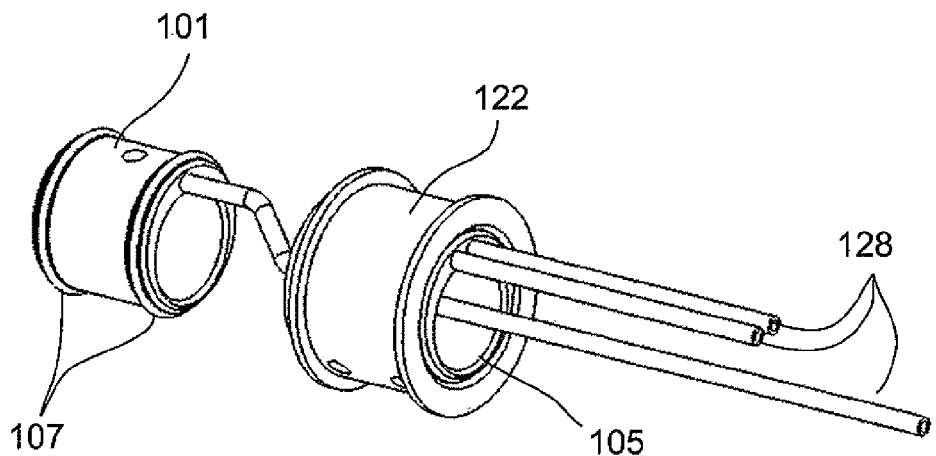
FIG. 1B is a perspective view of a front main body with gaskets and a rear main body coaxially mounted with a rear balloon housing of a balloon type probe apparatus adapted with a spring in a retracted configuration, in accordance with an exemplary embodiment of the invention.

FIG. 1B shows a perspective view of front main body 101 with gaskets 107 and rear main body 105 coaxially mounted with a rear balloon housing 122 of probe apparatus 100, in accordance with an exemplary embodiment of the invention. It should be understood that front main body 101 has fitted thereon a front balloon housing 112 and rear main body 105 has fitted thereon at least one gasket between rear main body 105 and rear balloon housing 122, in an exemplary embodiment of the invention, however the front and rear are each shown only in partial detail for explanatory purposes (i.e. the front without a housing and in the rear the gaskets are covered by housing 122). In an embodiment of the invention, housing 112, 122 is made of any material which is rigid enough to twist in the lumen without substantially losing its shape. In an embodiment of the invention, the housing is made of plastic. In some embodiments of the invention, the housing is made of metal. Optionally, the housing is biocompatible.

In an embodiment of the invention, gaskets 107 are adapted to enable housings 112, 122 and/or balloons 110, 120 to rotate around their respective main bodies 101, 105, for example by being secured to main bodies 101, 105 but not to housings 112, 122 and/or by being constructed of a material which will prevent leakage of inflation material but still be slidable with respect to housings 112, 122.

Figure 1C:
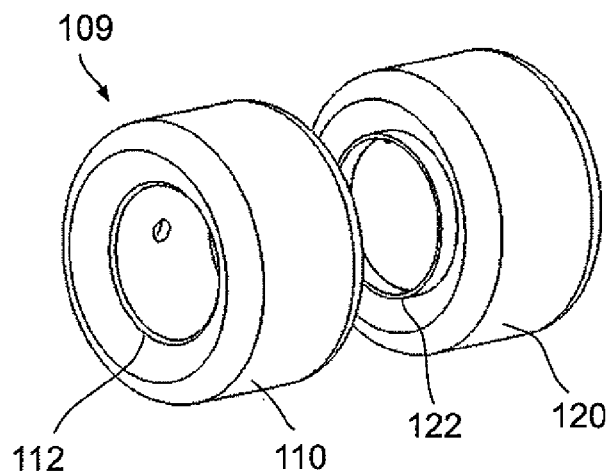
FIG. 1C is a perspective view of the probe apparatus of FIG. 1B without front and rear main bodies for clarity but with front and rear balloons mounted on their respective housings, in accordance with an exemplary embodiment of the invention.

FIG. 1C is a perspective view of probe apparatus 100 of FIG. 1B without front 101 and rear 105 main bodies for clarity but with front 110 and rear 120 balloons mounted on their respective housings 112, 122, in accordance with an exemplary embodiment of the invention. Front balloon section 109 includes front balloon 110 which is selectively inflatable and/or deflatable, in some embodiments of the invention. Front balloon 110, in an exemplary embodiment of the invention, is located on the forward side of probe apparatus 100, that is, the side inserted into the lumen first. In an embodiment of the invention, front balloon 110 is flexible. Front balloon 110 is substantially and/or loosely located on front balloon housing 112 which is also included in front balloon section 109, in an exemplary embodiment of the invention. Front balloon housing 112 is attached to the forward side of advancement balloon section 103, shown and described in more detail with respect to FIG. 1E.

Probe apparatus 100 includes rear balloon section 118 which, in an embodiment of the invention, is comprised of rear main body, 105, rear balloon 120 and/or rear balloon housing 122. Rear balloon 120 performs and/or is constructed similarly to front balloon 110, in an embodiment of the invention.

Figure 1D:
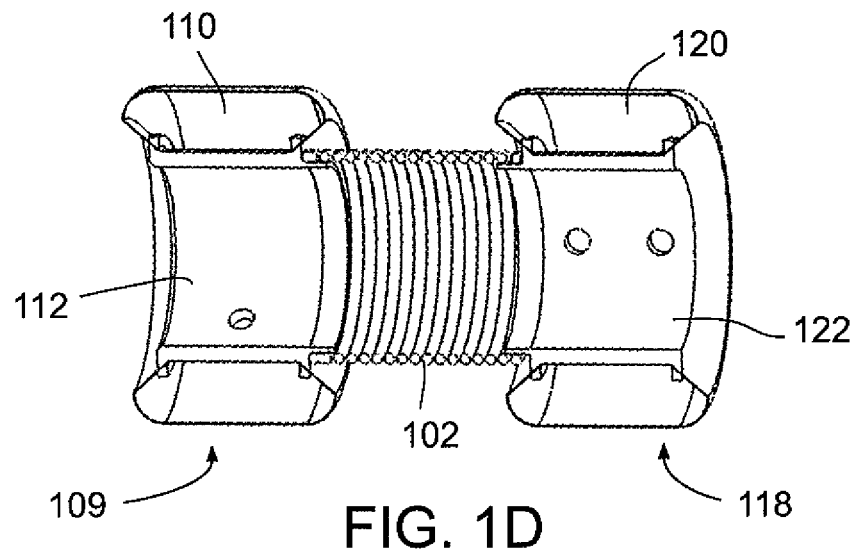
FIG. 1D is a cross-sectional, perspective view of FIG. 1C and including a spring, in accordance with an exemplary embodiment of the invention.

FIG. 1D is a cross-sectional, perspective view of probe apparatus 100 of FIG. 1C and including a spring 102, in accordance with an exemplary embodiment of the invention. Spring 102 is adapted for retracting advancement balloon 104 and/or for twisting at least one of front balloon section 109, advancement balloon section 103 and rear balloon section 118, in some embodiments of the invention. Retracting and twisting are described in more detail with respect to FIG. 1E, inter alia.

Figure 1E:
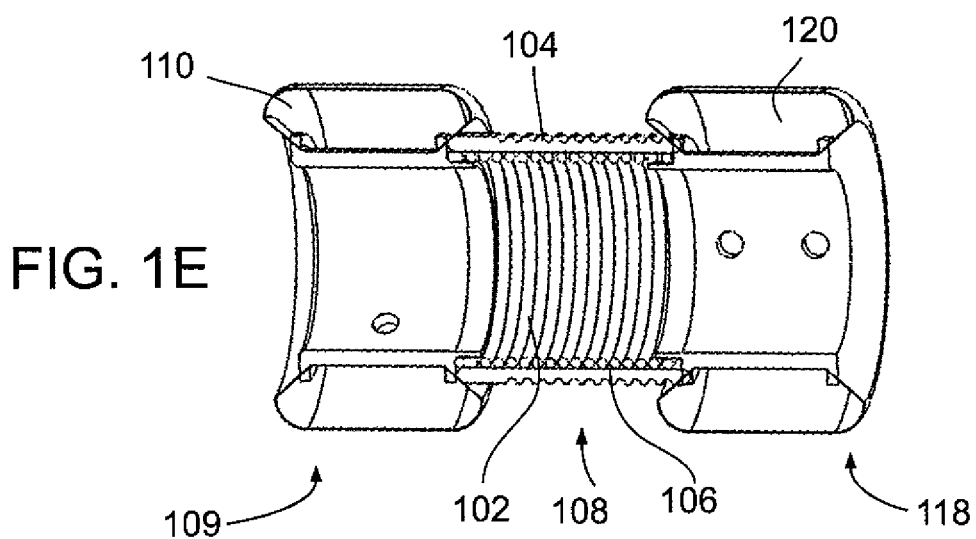
FIG. 1E is a cross-sectional, perspective view of the probe apparatus of FIG. 1D including an advancement balloon, in accordance with an exemplary embodiment of the invention.

FIG. 1E is a cross-sectional, perspective view of probe apparatus 100 of FIG. 1D including advancement balloon 104, in accordance with an exemplary embodiment of the invention. In an embodiment of the invention, advancement balloon 104 is a component of advancement balloon section 103 and is selectively inflatable and/or deflatable. In some embodiments of the invention, an inner circumference of advancement balloon 104 is defined by a sealing sleeve 106, shown in greater detail in FIG. 1F, which encloses inflation material, used to inflate advancement balloon 104, between sealing sleeve 106 and advancement balloon 104 and creating a void 108 within the interior of probe apparatus 100 that is not filled with inflation material during nominal use. In an embodiment of the invention, sealing sleeve 106 is a part of advancement balloon 104 that defines an inner circumference of advancement balloon 104. In some embodiments of the invention, advancement balloon 104 and/or sealing sleeve 106 are flexible and/or constructed of the same or similar materials. In an embodiment of the invention, at least one of balloons 104, 110, 118 is constructed of a biocompatible material. In some embodiments of the invention, at least one of balloons 104, 110, 118 is constructed from a flexible and/or elastic material, for example silicone, polyurethane, nylon, PVC and/or any material or combination of materials adapted for construction of inflatable structures.

In an embodiment of the invention, spring 102 is a tension type spring whereby the spring becomes longer under load. In a retracted configuration of probe apparatus 100, spring 102 is not under load, in an embodiment of the invention. In some embodiments of the invention, advancement balloon 104 is inflated causing movement of front balloon section 109 with respect to rear balloon section 118 and thus, loading spring 102. Deflation of advancement balloon 104 enables spring 102 to expend its energy by retracting advancement balloon 104 and bringing front balloon section 109 and rear balloon section 118 closer together, in an exemplary embodiment of the invention.

In an embodiment of the invention, twisting at least one of front balloon section 109, advancement balloon section 103 and rear balloon section 118 is an advantage over many currently practiced solutions. Conventional, non-twisting methodologies often result in the tip of a probe apparatus digging into and/or getting caught on the lumen wall, whereas the twisting or screwing motion of the presently described probe apparatuses maintains the probe apparatus centrally situated in the lumen during nominal operation. In an embodiment of the invention, the twisting motion also reduces the pulling and/or stretching applied to the lumen by non-twisting devices. In some embodiments of the invention, at least one of balloons 104, 110, 118 is twisted up to 90 degrees during a movement cycle. Optionally, at least one of balloons 104, 110, 118 is twisted up to 180 degrees during a movement cycle. In some embodiments of the invention, at least one of balloons 104, 110, 118 is twisted up to 360 degrees during a movement cycle.

In an embodiment of the invention, spring 102 and/or advancement balloon 104 is biased with a torsion force and as advancement balloon 104 extends and/or retracts spring 102 applies twisting forces to advancement balloon section 103 causing twisting of at least one of front balloon section 109, advancement balloon section 103 and rear balloon section 118, in some embodiments of the invention. Exemplary movement cycles including retraction and/or twisting are described and shown in more detail with respect to FIGS. 9A-F, 10 and/or 15.

In some embodiments of the invention, spring 102 is constructed of metal and/or a metal alloy. In some embodiments of the invention, the spring 102 is constructed of a plastic material. In an embodiment of the invention, spring 102 is a tubular structure coiled into a spring shape, the coiled tubular structure acting overall as a spring. Optionally, the tubular structure is comprised of plastic.

Figure 1F:
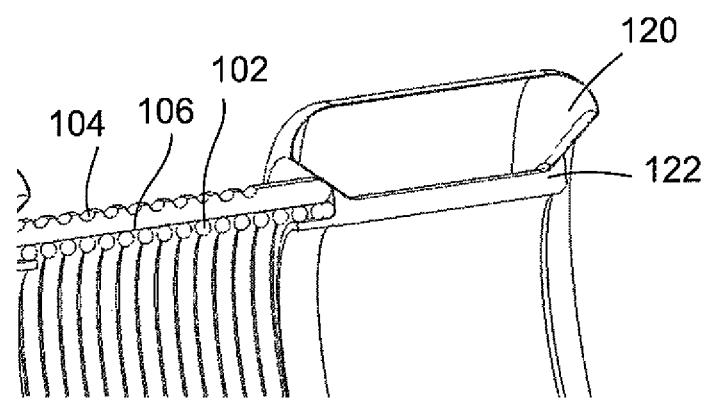
FIG. 1F is a detailed view of the relationship between rear balloon housing, advancement balloon, spring and rear balloon, in accordance with an exemplary embodiment of the invention.

FIG. 1F is a detailed view of the relationship between rear balloon housing 118, advancement balloon 104, spring 102 and rear balloon 120, in accordance with an exemplary embodiment of the invention. In an embodiment of the invention, rear balloon section 118 is attached to advancement balloon section 103 on the backward side of advancement balloon section 103 such that advancement balloon section 103 is located between front balloon section 109 and rear balloon section 118, in an axial arrangement. In some embodiments of the invention, the advancement balloon is connected to a housing 112, 122 using any one or a combination of heat welding, ultra-sonic welding, using an adhesive, using a solvent combining the housing with balloon material, and/or mechanically adhering the balloon to the housing, for example using snaps. In an embodiment of the invention, advancement balloon 104 and/or spring 102 are first connected to one of the housings 112, 122 and before connecting advancement balloon 104 to the other housing, balloon 104 and/or or spring 102 is twisted at least partially during manufacture. Upon connecting balloon 104 and/or spring 102 to the other housing, advancement balloon 104 remains twisted while spring 102 returns to an untwisted condition. In an embodiment of the invention, spring 102 is located on the interior of sealing sleeve 106 and/or extends substantially the length of advancement balloon section 103.

Figure 1G:
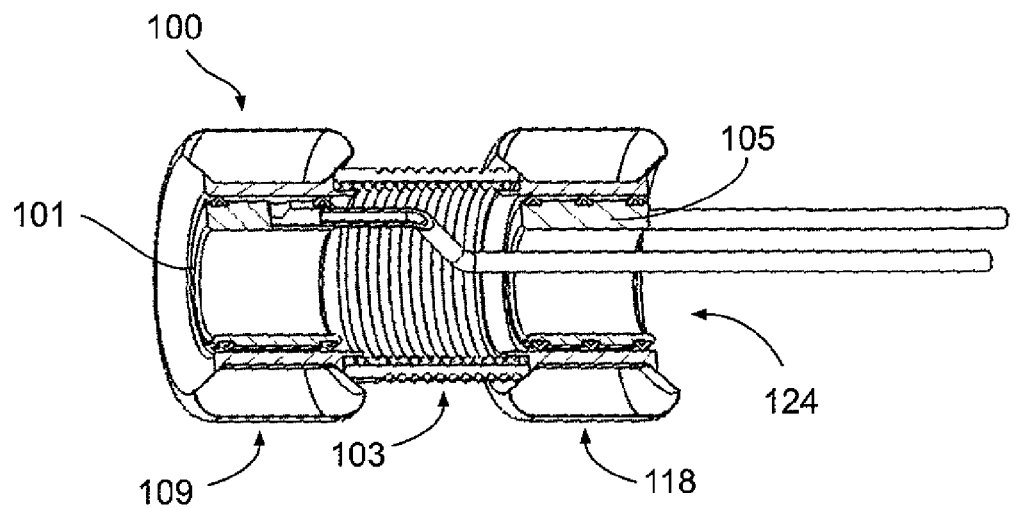
FIG. 1G is a cross-sectional, perspective view of a probe apparatus of FIG. 1E showing front and rear main bodies, in accordance with an exemplary embodiment of the invention.
Figure 1H:
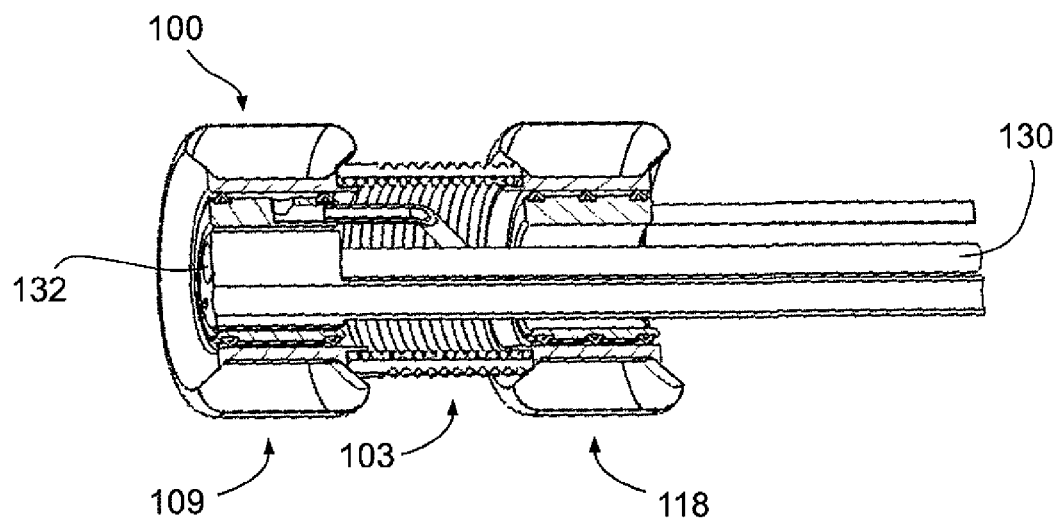
FIG. 1H is a cross-sectional, perspective view of a probe apparatus of FIG. 1G showing at least one medical instrument and/or a supply line placed in an instrument channel, in accordance with an exemplary embodiment of the invention.

In an embodiment of the invention, probe apparatus 100 is adapted to be used with medical diagnostic or treatment instruments, for example by being provided with an instrument channel 124, shown in FIG. 1G, which traverses the length of probe apparatus 100 enabling instruments to be threaded into probe apparatus 100 via rear balloon section 118, advancement balloon section 103 and front balloon section 109. In an embodiment of the invention, instrument channel 124 has a tubular shape. In some embodiments of the invention, the instrument channel 124 enables at least one medical instrument to extend out from probe apparatus 100 and into the lumen. In some embodiments of the invention, a supply line 130 containing at least one medical instrument 132 and/or supply element (e.g. electricity, inflation material) is inserted through instrument channel 124, as shown in FIG. 1H. In an embodiment of the invention, at least one medical instrument 132 includes a camera and/or a light source. Optionally, the at least one medical instrument 132 is any commercially available endoscope and/or lumen-insertable device. In an embodiment of the invention, at least one medical instrument 132 and/or supply line 130 is removably affixed in instrument channel 124, for example by at least one snap. Optionally, the at least one medical instrument and/or supply line 130 is removably fastened to front main body 101.

Figure 2A:
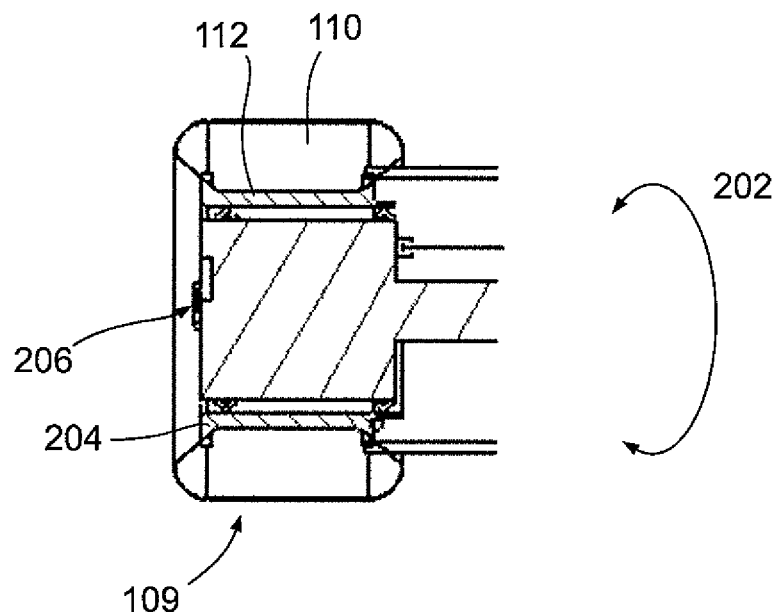
FIG. 2A is a cross-sectional view showing a front balloon housing of probe apparatus adapted for prevention of the supply line in an instrument channel from becoming twisted, in accordance with an exemplary embodiment of the invention.

As described elsewhere herein, movement of probe apparatus 100 translates to movement of at least one medical instrument 132 located therein, in accordance with some exemplary embodiments of the invention. In an embodiment of the invention, the supply line 130 within instrument channel 124 rotates freely with respect to sections 103, 109, 118 such that during twisting of at least one section 103, 109, 118, supply line 130 remains relatively untwisted, as shown and described in more detail with respect to FIG. 2A. In some embodiments of the invention, probe apparatus 100 is used with any of a number of medical instruments known to those in the art to provide movement to those instruments.

As described elsewhere herein, probe apparatus 100 is adapted to enable at least one of front balloon 110, advancement balloon 104 and/or rear balloon 120 to be selectively inflatable and/or deflatable. For example, inflation material supply lines 128 are provided to at least one of front balloon 110, advancement balloon 104 and/or rear balloon 120 through which an inflation material is transported in and/or out for inflation and/or deflation, respectively, of at least one balloon 110, 104, 120. An exemplary supply line 128 configuration is shown in FIG. 1A, however just about any configuration which is adapted to provide selective inflation and/or deflation to at least one of balloons 110, 104 and 120 can be used. In an embodiment of the invention, supply line 130 is operationally connected to supply line 128 and main bodies 101, 105, wherein inflation material transits to at least one balloon 104, 110, 120 via supply lines 128, 130 and at least one main body 101, 105. Supply lines 128 are provided with inflation material from at least one reservoir of inflation material outside the lumen and/or patient's body, in some embodiments of the invention. In an embodiment of the invention, inflation material is air. Optionally, inflation material is a liquid, for example water or saline solution. In some embodiments of the invention, at least one balloon section 103, 109, 118 is provided with a pressure relief mechanism such as a pressure activated gasket. In an embodiment of the invention, at least one gasket 107 is used retain inflation material in the probe apparatus.

In some embodiments of the invention, at least one component of probe apparatus 100 is disposable, for example at least one supply line 128, 130 and/or at least one balloon 110, 104, 120, and/or at least one medical instrument such that probe apparatus 100 is reusable and/or at least partially disposable.

It should be understood that probe apparatus 100 of FIGS. 1A-1H is shown in a retracted configuration. In an embodiment of the invention, an extended configuration of probe apparatus 100 is attained by inflating advancement balloon 104, as described above. Other exemplary extended configurations are shown and described with respect to other embodiments below.

As briefly described above, FIG. 2A is a cross-sectional view showing front balloon housing 112 of probe apparatus 100 adapted for prevention of twisting of at least one supply line 130, in accordance with an embodiment of the invention. At least one supply line 130 is adapted to resist twisting by being passed through housing 112 with the ability to rotate 202 independently from housing 112, in an embodiment of the invention. Independent rotational ability of supply line 130 reduces the chance of unwanted twisting of supply line 130 during the movement cycle, an exemplary movement cycle described with respect to FIGS. 9A-F. A lip 204 is provided to supply line 130 to ensure that a distal opening 206 of supply line 130 is always located forward of front balloon housing 112.

Figure 2B:
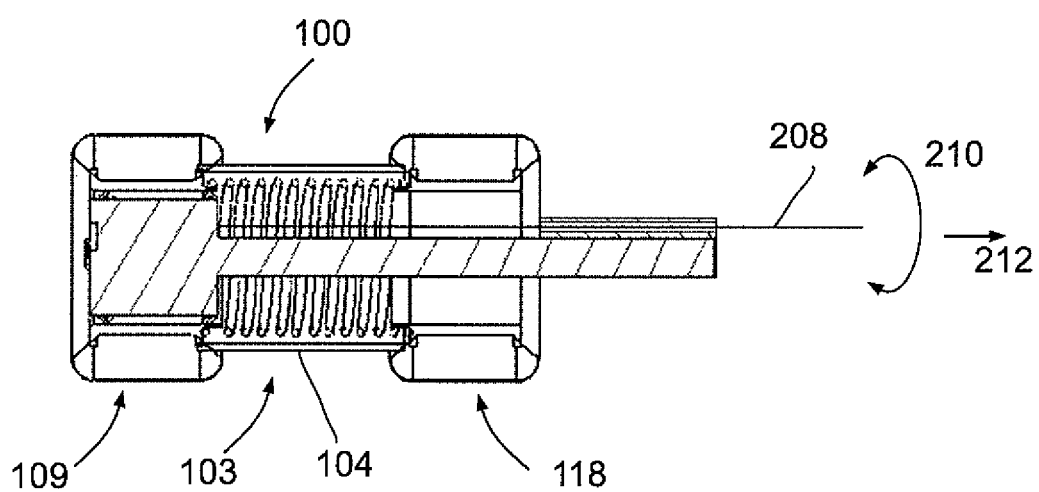
FIG. 2B is a cross-sectional view of a balloon type probe apparatus adapted to include a torque resistant cable, in accordance with an exemplary embodiment of the invention.

In some embodiments of the invention, a torque resistant cable 208, shown in FIG. 2B, is provided to probe apparatus 100 for providing rotation to front balloon section 109 and/or for providing retraction of the advancement balloon 104. In an embodiment of the invention, torque resistant cable 208 is affixed to the front balloon section 109 and/or at least one medical instrument such that when cable 208 is pushed "forward" in a distal direction and/or when cable 208 is pulled "backward" in a proximal direction it causes rotation 210 of at least one component of section 109 and/or section 103 and/or section 118 because the pushing and/or pulling simulate the inflation and/or deflation of advancement balloon 104, in an embodiment of the invention. In an embodiment of the invention, pushing cable 208 in a distal direction extends front balloon section 109 away from rear balloon section 118, expanding advancement balloon section 103 linearly and/or causing an overall extension of probe apparatus 100. In an embodiment of the invention, pulling cable 208 in a proximal direction 212 draws front balloon section 109 closer to rear balloon section 118, collapsing advancement balloon section 103 and/or causing an overall retraction of probe apparatus 100.

In an embodiment of the invention, components that rotate 210 include at least one of housing 112 and/or balloon 110 which rotate together around main body 101 in the case of pushing forward and/or at least one of housing 122 and/or balloon 120 which rotate around main body 105 in the case of pulling backward.

In an embodiment of the invention, cable 208 is comprised of a metal alloy, for example nitinol. Optionally, cable 208 is constructed of a plastic material. In some embodiments of the invention, cable 208 is inserted through instrument channel 124. In some embodiments of the invention, cable 208 is inserted into probe apparatus 100 in a dedicated cable channel, such as shown in FIG. 2B.

Figure 3A:
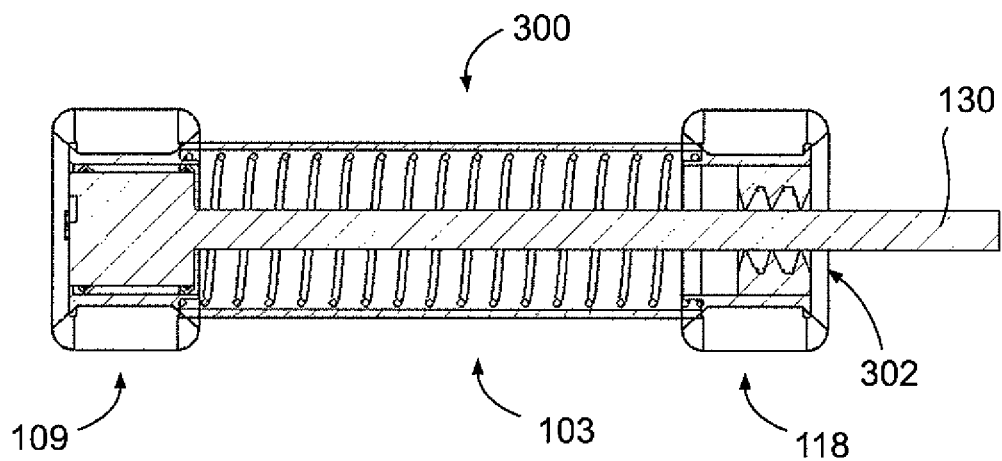
FIG. 3A is a cross-sectional view of a balloon type probe apparatus in an extended configuration and adapted for use with a sliding gasket, in accordance with an exemplary embodiment of the invention.
Figure 3B:
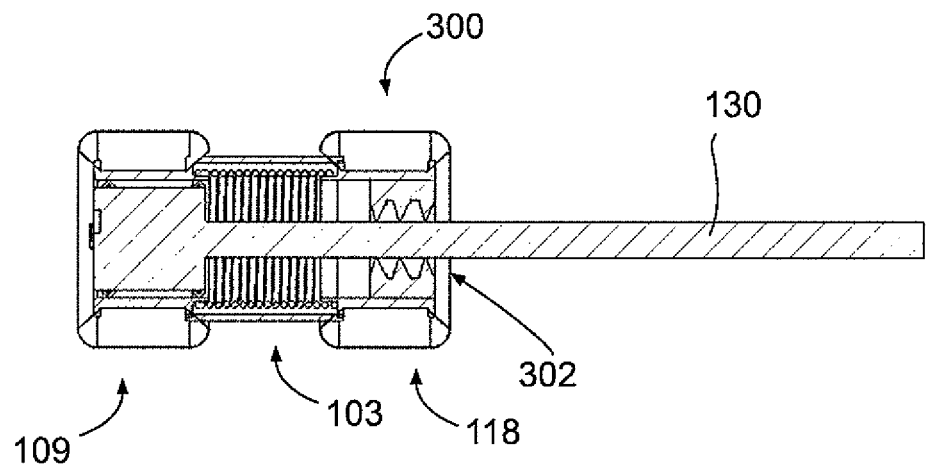
FIG. 3B is a cross-sectional view of a balloon type probe apparatus in an retracted configuration and adapted for use with a sliding gasket, in accordance with an exemplary embodiment of the invention.

FIG. 3A shows a cross-sectional view of a balloon type probe apparatus 300 in an extended configuration and adapted for use with a sliding gasket 302, in accordance with an exemplary embodiment of the invention. In some embodiments of the invention, probe apparatus 300 differs in essence from probe apparatus 100 in that there is no sealing sleeve 106 to trap inflation material between the sleeve 106 and advancement balloon 104, thus sliding gasket 302 is used to prevent leakage (or at least significant leakage) of inflation material out of advancement balloon section 103 but still allow supply line 130 to slide relatively freely with respect to sections 109, 103 and/or 118 during extension and/or retraction of probe apparatus 300. In some embodiments of the invention, supply line 130 prevents leakage of inflation material into a lumen of supply line 130. In an embodiment of the invention, sliding gasket is constructed of any material used in the gasket manufacturing art, for example, rubber, silicon or polyurethane. FIG. 3B is a cross-sectional view of probe apparatus 300 in a retracted configuration, in accordance with an exemplary embodiment of the invention. In some embodiments of the invention, inflation material is extracted via at least one supply tube 128 during retraction. Optionally, pressure within an inflated balloon pushes inflation material out of supply tube 128 during retraction. Optionally, evacuation of inflation material is performed or assisted by vacuum suction on supply tube 128. In an embodiment of the invention supply 130 tube has fluid communication with the interior of the lumen. Optionally, at least one supply tube 128, 130 is used to apply vacuum suction for removal of material from the lumen.

Figure 4A:
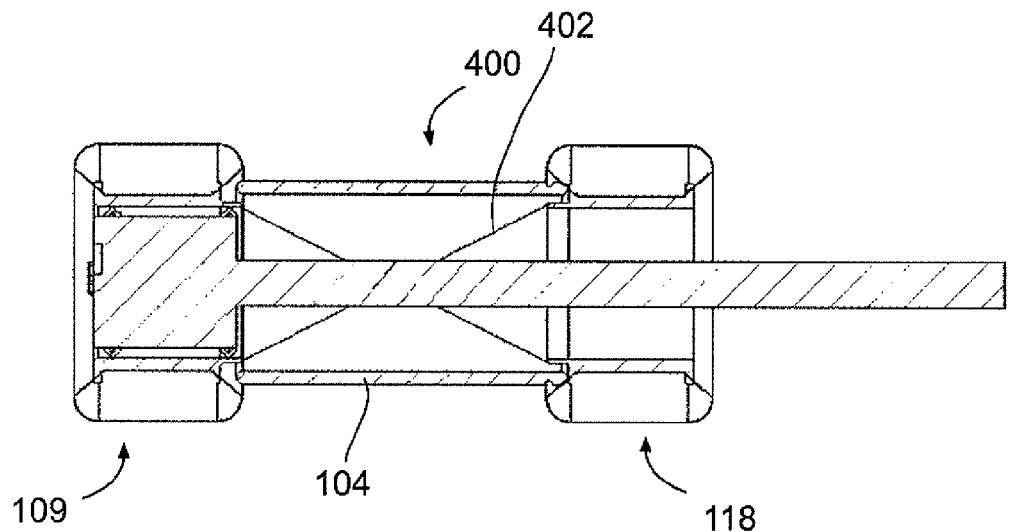
FIG. 4A is a cross-sectional view of a balloon type probe apparatus adapted with an elastic band in an extended configuration, in accordance with an exemplary embodiment of the invention.

FIG. 4A is a cross-sectional view of a balloon type probe apparatus 400 adapted with a different twisting element from probe apparatus 100, for example at least one elastic band 402, in an extended configuration, in accordance with an exemplary embodiment of the invention. In an embodiment of the invention, probe apparatus 400 differs in essence from probe apparatus 100 in that at least one elastic band 402 is used in lieu of spring 102 using the elasticity of the at least one elastic band 402 and/or inflation pressure to provide retraction and/or twisting forces. In an embodiment of the invention, the at least one elastic band 402 is loaded when probe apparatus 400 is in an extended configuration such that upon deflation of advancement balloon 104 the at least one elastic band 402 urges front balloon section 109 and/or rear balloon section 118 closer together as the at least one elastic band 402 expends energy.

Figure 4B:
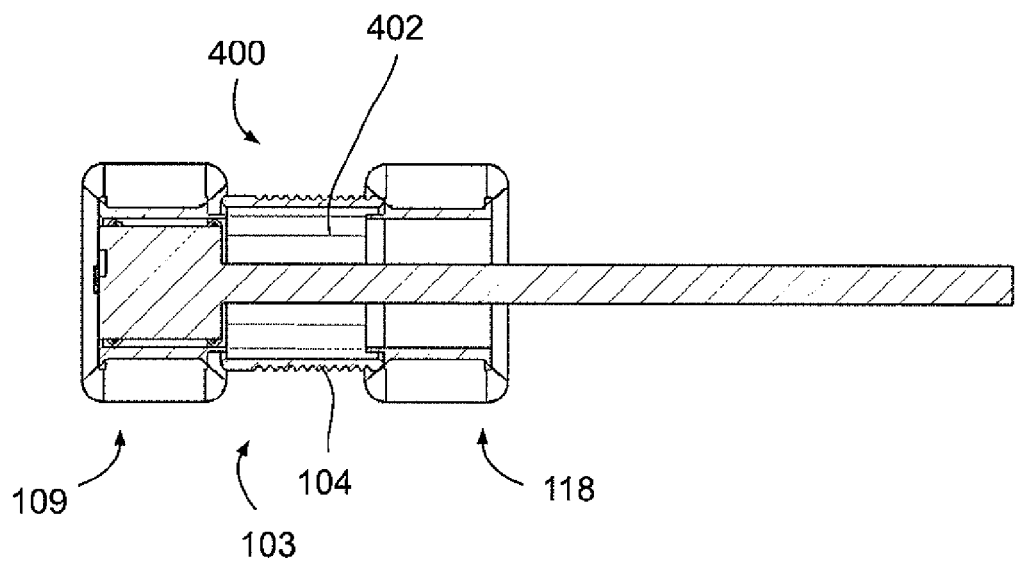
FIG. 4B is a cross-sectional view of a balloon type probe apparatus adapted with an elastic band in a retracted configuration, in accordance with an exemplary embodiment of the invention.

FIG. 4B is a cross-sectional view of probe apparatus 400 and at least one elastic band 402 in a retracted configuration, in accordance with an exemplary embodiment of the invention. It should be noted that in the retracted configuration, the at least one elastic band 402 is straight, in accordance with an exemplary embodiment of the invention. As advancement balloon 104 extends under inflation, the at least one elastic band 402 stretches, twisting at least advancement balloon section 103 as the band 402 twists. In some embodiments of the invention, the at least one elastic band 402 is twisted during manufacture.

Figure 5A:
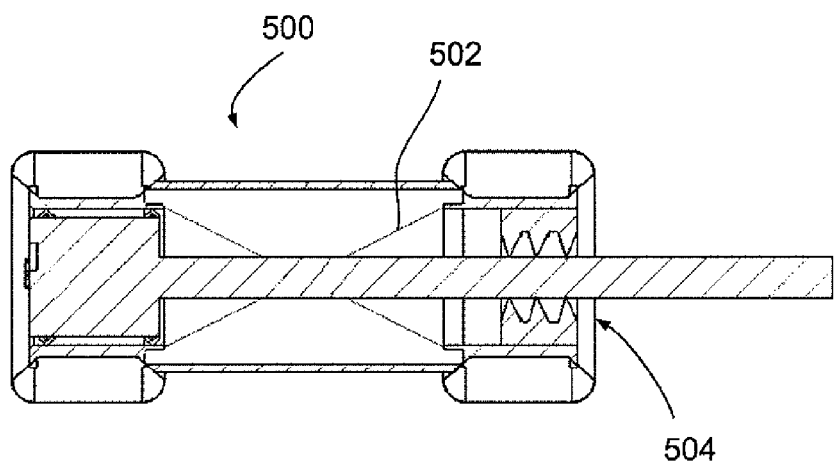
FIG. 5A is a cross-sectional view of a balloon type probe apparatus adapted with an elastic band and a sliding gasket in an extended configuration, in accordance with an exemplary embodiment of the invention.
Figure 5B:
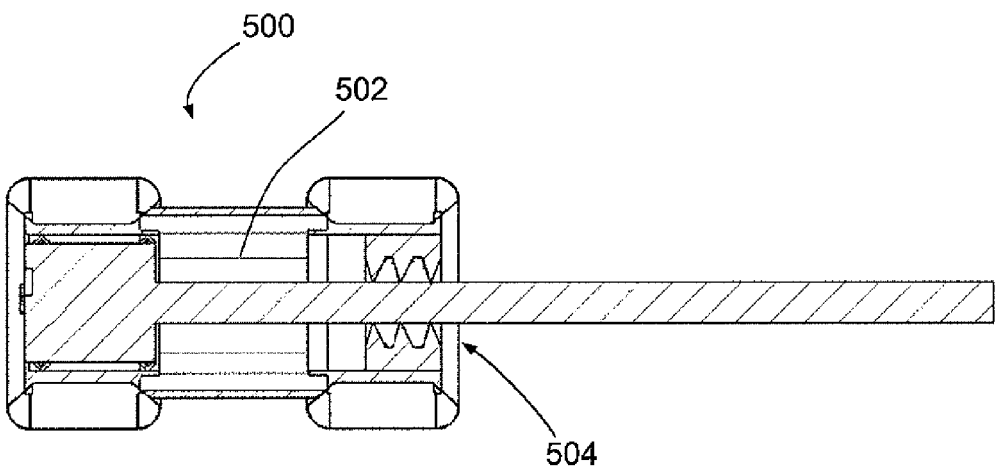
FIG. 5B is a cross-sectional view of a balloon type probe apparatus adapted with an elastic band and a sliding gasket in a retracted configuration, in accordance with an exemplary embodiment of the invention.

FIGS. 5A and 5B are cross-sectional views of a balloon type probe apparatus 500 adapted with at least one elastic band 502 and a sliding gasket 504, in accordance with an exemplary embodiment of the invention. FIG. 5A shows probe apparatus 500 in an extended configuration and FIG. 5B shows probe apparatus 500 in a retracted configuration, in accordance with an exemplary embodiment of the invention. In some exemplary embodiments of the invention, probe apparatus 500 borrows operational characteristics of probe apparatuses 300 (sliding gasket) and 400 (at least one elastic band).

Figure 6A:
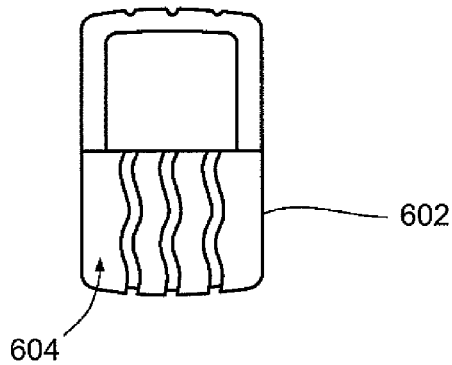
FIGS. 6A-D are partial cross-sectional or cross-sectional views of a balloon adapted for use with a balloon type probe apparatus, in accordance with an exemplary embodiment of the invention.
Figure 6B:
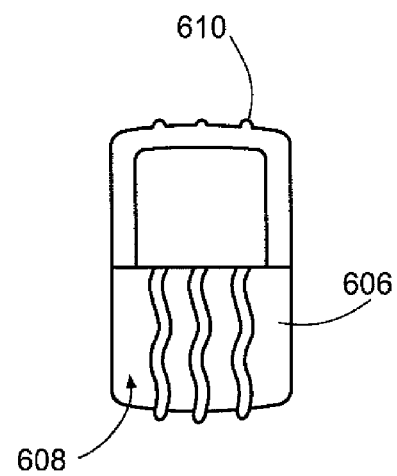
Figure 6C:
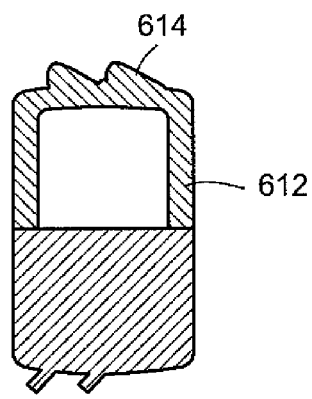

FIGS. 6A-D are cross-sectional or partial cross-sectional views of balloons adapted for use with a balloon type probe apparatus, in accordance with an exemplary embodiment of the invention. FIG. 6A is a partial cross-sectional view of a balloon 602 which has a surface texture 604 adapted to interface with the inner surface of a lumen, in an embodiment of the invention. Surface texture 604 comprises a series of furrows, in an embodiment of the invention. FIG. 6B is a balloon 606 with a variation 608 of surface texture 604 which includes enhancements to the peaks 610 of the furrows to enhance interdigitation of the furrows with features present on the surface of the lumen, in accordance with an exemplary embodiment of the invention. FIG. 6C is a partial cross-sectional view of a balloon 612 with at least one thread 614 on its surface to enhance the advancement of a probe apparatus while the front balloon is rotated against the lumen as the advancement balloon is inflated. In an embodiment of the invention, the thread 614 is biased to enhance forward movement.

Figure 6D:
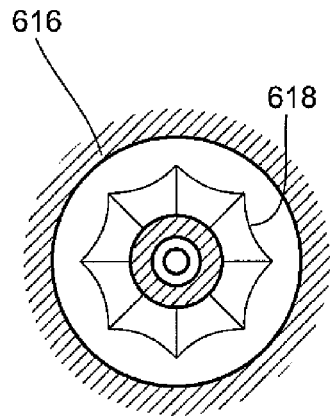

FIG. 6D is a lateral cross-sectional view of a lumen 616 and a front balloon 618 comprising a serrated shape adapted to enhance the interdigitation of the balloon 618 to the inner surface of the lumen 616 while the front balloon 618 is expanded.

Figures 7A, 7B:
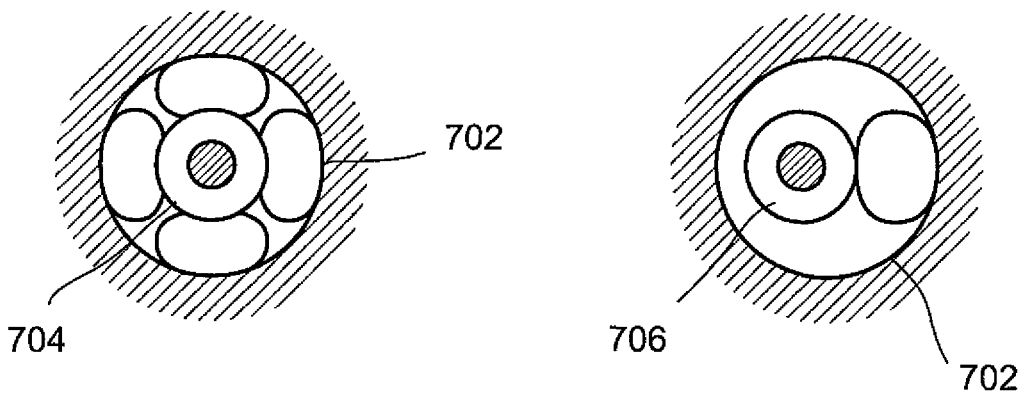
FIGS. 7A-7B are cross-sectional views of a lumen and a balloon type probe apparatus located various balloon deployment configurations, in accordance with exemplary embodiments of the invention.

By using a probe apparatus with a plurality of independently inflatable and/or deflatable balloons associated with a balloon section, the orientation of the probe apparatus can be altered with respect to the lumen. It should be noted that the front and/or rear balloon is replaced by a plurality of independently inflatable and/or deflatable balloons, in an embodiment of the invention. The attending medical professional using the probe apparatus uses a camera, for example an endoscope, to decide which balloon should be inflated to position the probe apparatus as desired, in an embodiment of the invention. Selectively inflating balloons is a method of deflecting the tip of the probe apparatus, for example for performing a procedure on the lumen wall, in an embodiment of the invention. In some embodiments of the invention, maneuvering the probe apparatus using a plurality of independently inflatable and/or deflatable balloons provides a mechanism for navigating curves in the lumen. Referring to FIGS. 7A-B, lateral cross-sectional views of a lumen 702 and probe apparatuses 704, 706 located therein in various balloon deployment configurations are shown, in accordance with exemplary embodiments of the invention. FIG. 7A shows a probe apparatus 704 with at least 4 balloons evenly inflated to position the probe apparatus centrally in lumen 702. FIG. 7B shows a probe apparatus 706 where one balloon is inflated, biasing probe apparatus 706 away from the inflated balloon in the lumen 702.

Figure 8:
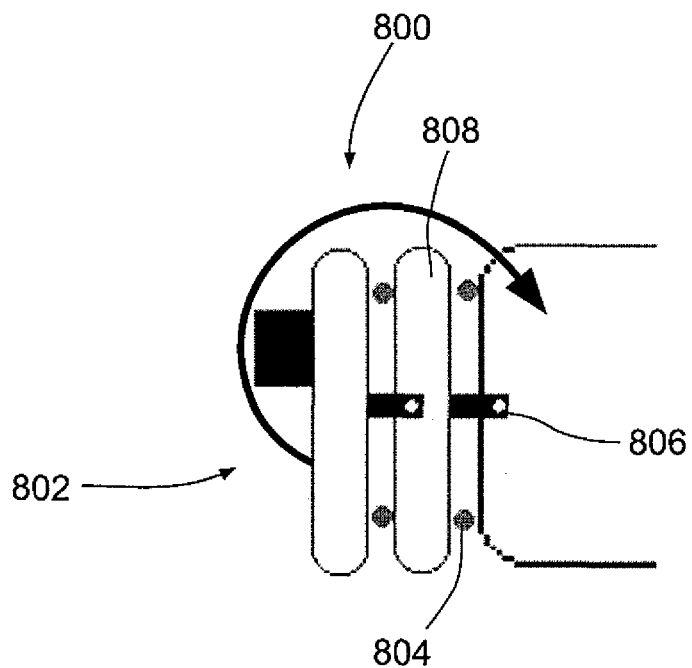
FIG. 8 is a side view of a balloon type probe apparatus with a jointed tip, in accordance with an exemplary embodiment of the invention.

FIG. 8 is a side view of a balloon type probe apparatus 800 adapted to deflect a probe tip 802 using at least one independently inflatable and/or deflatable balloon 804 in combination with at least one joint 806, in accordance with an exemplary embodiment of the invention. In an embodiment of the invention, balloon 804 is inflated causing a plate 808 to angle away from balloon 804 and/or a front or rear balloon section at joint 806. In an embodiment of the invention, plate 808 is a selectably inflatable and/or deflatable balloon. In some embodiments of the invention, additional plates and/or joints and/or balloons are used to increase radius of curvature to tip 802. For example, as shown in FIG. 8, an additional level of balloon/plate is shown which when the additional balloon is inflated will cause tip 802 to deflect more, in an embodiment of the invention.

In an embodiment of the invention, probe apparatus 800 is provided with an instrument channel which extends through tip 802 to allow operation of apparatus 800 in conjunction with at least one medical instrument located therein. In an embodiment of the invention, tip 802 is deflected to ease navigation of probe apparatus 800 through a lumen and/or to provide access to the inner surface of the lumen to the at least one medical instrument.

In some embodiments of the invention, a balloon which bends in a predetermined fashion when inflated is used in lieu of or in addition to the hinge-joint 806 described above. Optionally, a plurality of balloons each of which exhibits a different degree of bending is offered for selection to a probe apparatus operator for performing a procedure.

Figure 15:
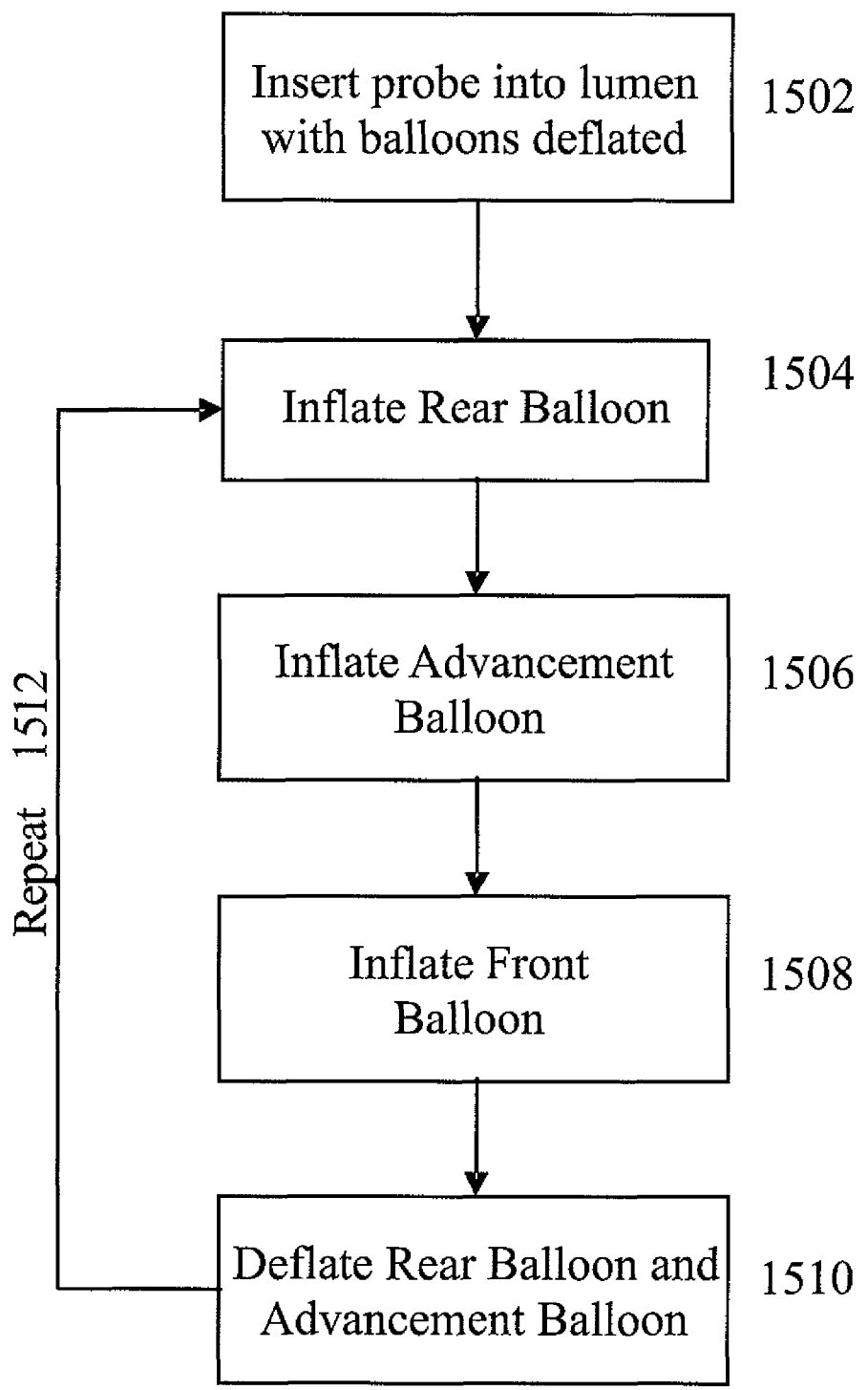
FIG. 15 is a flowchart depicting a method of use for a balloon type probe apparatus, in accordance with an exemplary embodiment of the invention; and, FIG. 16 is a flowchart depicting a method of navigating a curve in a lumen, in accordance with an exemplary embodiment of the invention.

FIGS. 9A-9F are illustrations of segments of a movement cycle of a balloon type probe apparatus 900, in accordance with an exemplary embodiment of the invention. In some embodiments of the invention, probe apparatus 900 is any one of probe apparatuses 100, 300, 400, 500, 704, 706, 800 and/or any other balloon type probe apparatus described herein. Exemplary movement depicted in FIGS. 9A-9F is also described and shown with respect to FIG. 15.

Figure 9A:
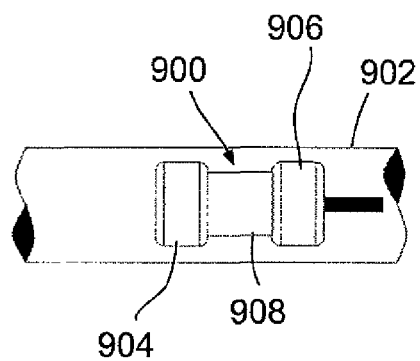
FIGS. 9A-F are illustrations of a movement cycle of a balloon type probe apparatus, in accordance with an exemplary embodiment of the invention.

FIG. 9A shows probe apparatus 900 inserted (1502) into a lumen 902 with front 904, advancement 908 and rear 906 balloons in a deflated state, in an embodiment of the invention. In an embodiment of the invention, the outer diameter of balloons 904, 906 and 908 in a deflated state is less than the inner diameter of the lumen 902.

Figure 9B:
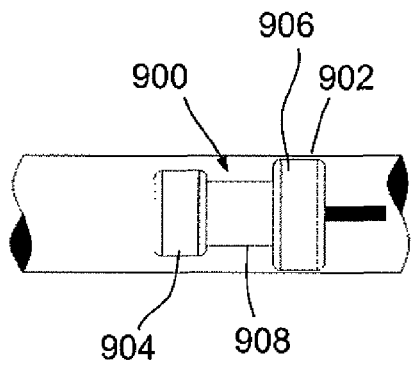

FIG. 9B shows probe apparatus 900 with rear balloon 906 inflated (1504) substantially securing probe apparatus 900 in place within lumen 902, in an exemplary embodiment of the invention.

Figure 9C:
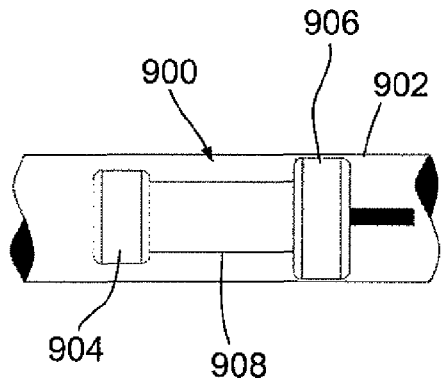

FIG. 9C shows probe apparatus 900 with rear balloon 906 inflated and advancement balloon 908 at least partially inflated, in accordance with an exemplary embodiment of the invention. In an embodiment of the invention, as advancement balloon 908 inflates (1506), front balloon 904 moves forward into lumen 902 and away from rear balloon 906. In some embodiments of the invention, at least one of front balloon 904 and/or advancement balloon 908 rotate/twist, such as described elsewhere herein, as advancement balloon 908 inflates forward into lumen 902.

Figure 9D:
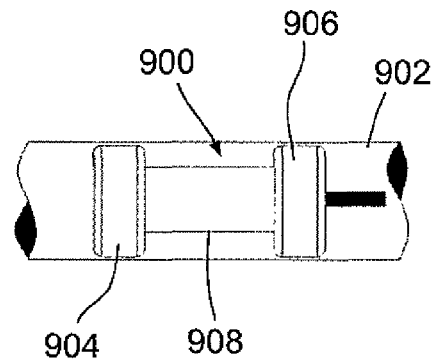

FIG. 9D shows probe apparatus 900 with rear balloon 906, advancement balloon 908 at least partially inflated and front balloon 904 inflated (1508), in accordance with an exemplary embodiment of the invention. In an embodiment of the invention, front balloon substantially secures probe apparatus 900 to the inner circumference of lumen 902 regardless of the securing effectuated by rear balloon 906.

Figure 9E:
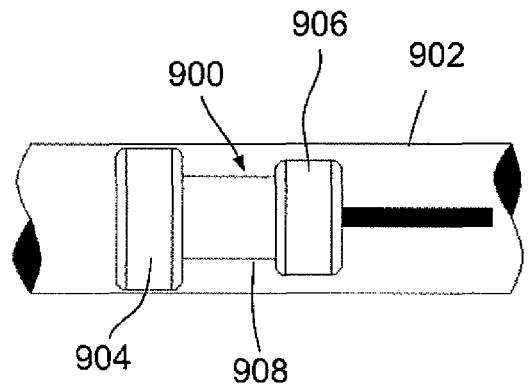

FIG. 9E shows probe apparatus 900 with front balloon 904 substantially securing probe apparatus 900 to inner circumference of lumen 902 while rear balloon 906 and/or advancement balloon 908 are at least partially deflated (1510), causing at least a partial overall retraction of apparatus 900 as rear balloon 906 moves closer to front balloon 904, in accordance with an exemplary embodiment of the invention. In some embodiments of the invention, at least one of advancement balloon 908 and/or rear balloon 906 rotate/twist as retraction occurs.

Figure 9F:
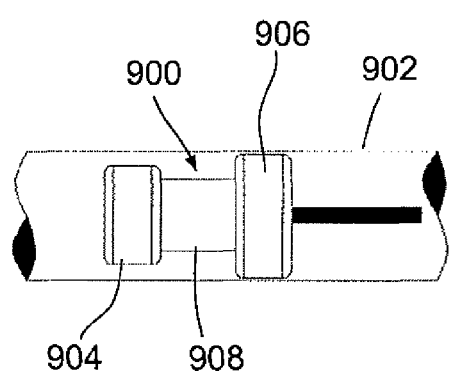

FIG. 9F shows the start (1512) of a new movement cycle after rear balloon 906 is re-inflated and front balloon 904 is deflated, to mirror the configuration of FIG. 9B and following the sequence shown in FIG. 9E, in accordance with an exemplary embodiment of the invention. It should be noted that backward motion of probe apparatus 900 is achieved by reversing the movement cycle, in an exemplary embodiment of the invention.

Figure 10:
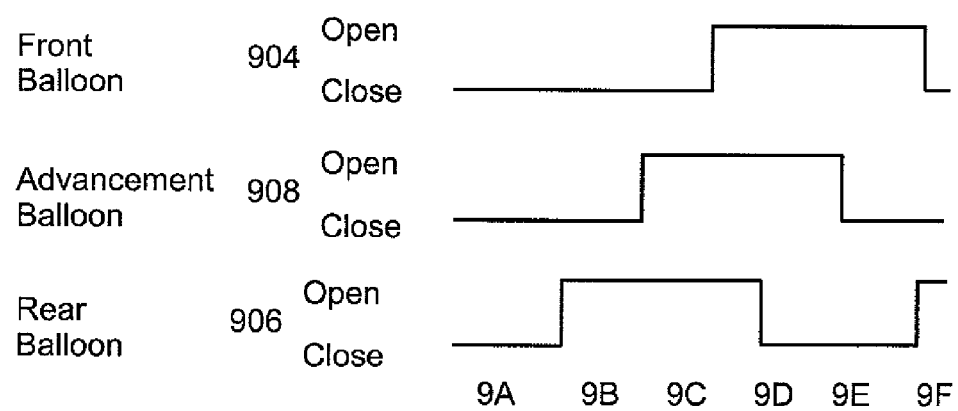
FIG. 10 is a graph demonstrating the status of the balloons of a balloon type probe corresponding to the phases of FIGS. 9A-F, in accordance with an exemplary embodiment of the invention.

FIG. 10 is a graph demonstrating the status of the balloons 904, 906, 908 of probe apparatus 900 corresponding to the phases of FIGS. 9A-F, in accordance with an exemplary embodiment of the invention.

Figure 16:
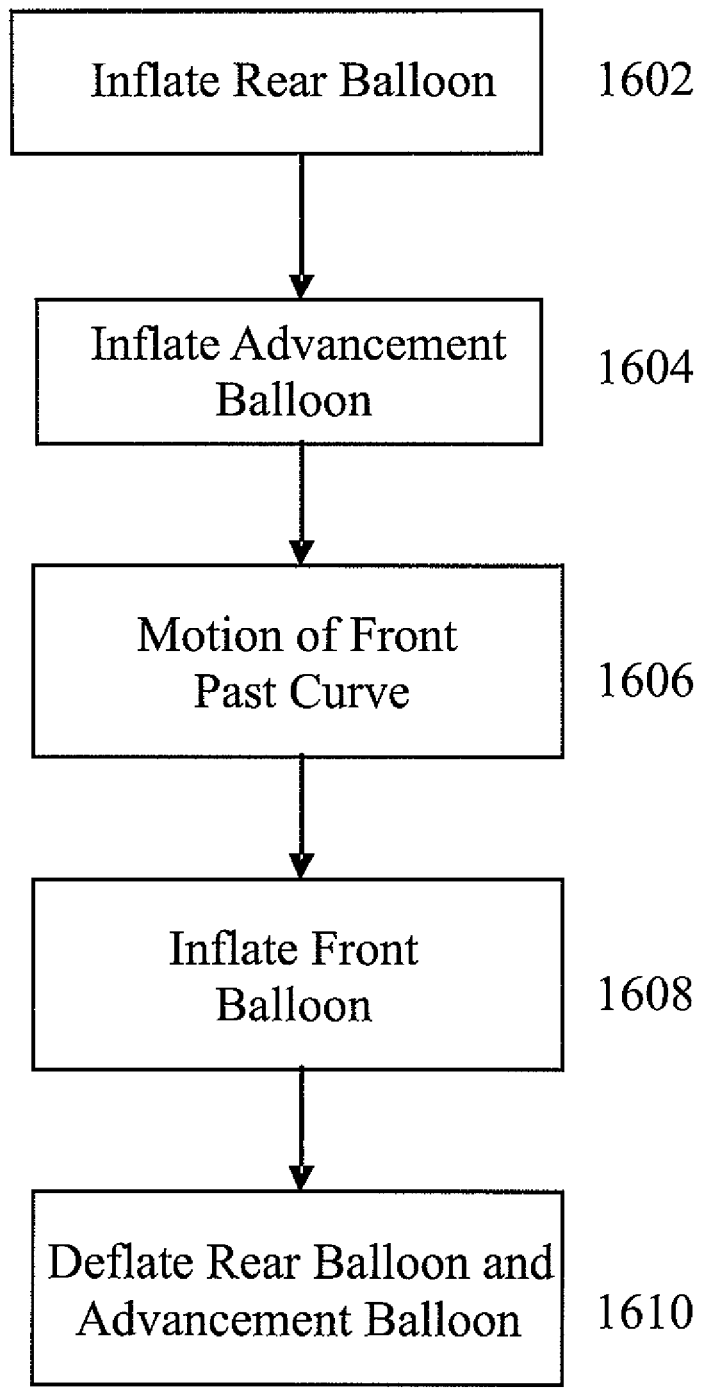

FIGS. 11A-11D are sequential illustrations of a balloon type probe apparatus 1100 navigating a curve in a lumen 1102, in accordance with an exemplary embodiment of the invention. Exemplary movement depicted in FIGS. 11A-11D is also described and shown with respect to FIG. 16.

Figure 11A:
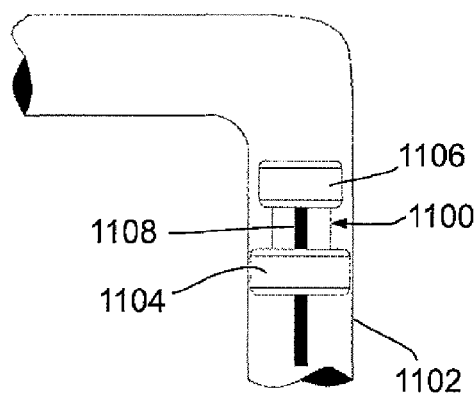
FIGS. 11A-D are sequential illustrations of a balloon type probe apparatus navigating a curve in a lumen, in accordance with an exemplary embodiment of the invention.
Figure 11B:
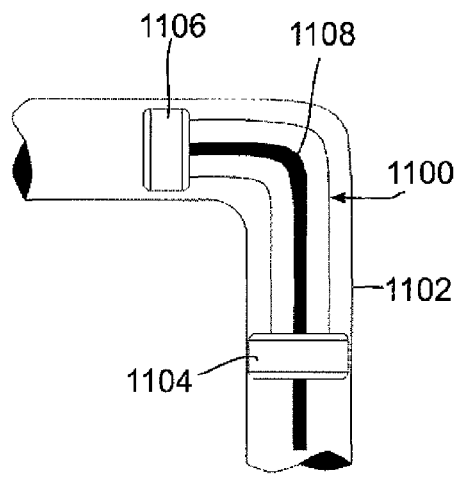
Figure 11C:
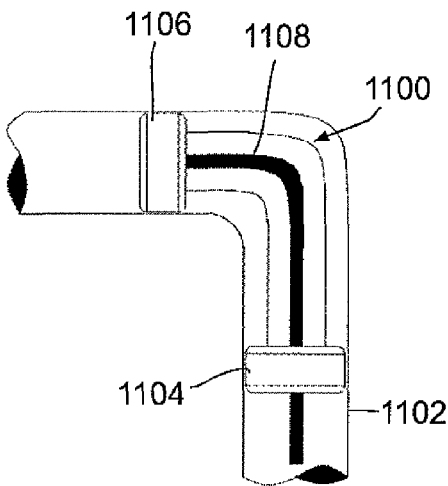
Figure 11D:
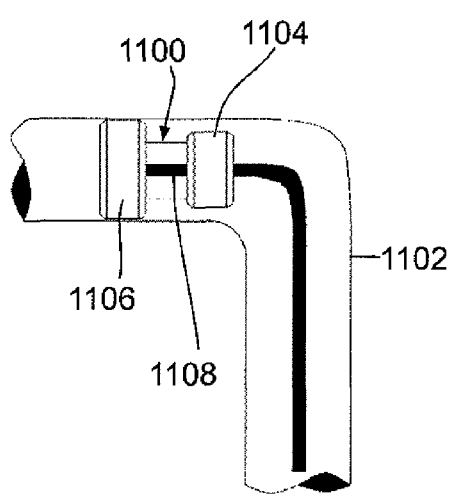

FIG. 11A shows probe apparatus 1100 already inserted in lumen 1102 with a rear balloon 1104 inflated (1602), substantially securing probe apparatus 1100 to an inner circumference of lumen 1102, in an exemplary embodiment of the invention. A front balloon 1106 and an advancement balloon 1108 of probe apparatus 1100 are at least partially deflated. FIG. 11B shows probe apparatus 1100 while rear balloon 1104 is still substantially secured to lumen 1102 with advancement balloon 1108 being at least partially inflated (1604), more inflated relative to FIG. 11A. In an embodiment of the invention, inflation (1604) of advancement balloon 1108 causes forward motion (1606) of front balloon 1106 around the curve in lumen 1102. In some embodiments of the invention, at least one of front balloon 1106 and/or advancement balloon 1108 rotates/twists during forward motion of advancement balloon 1108. FIG. 11C shows probe apparatus 1100 with both front balloon 1106 inflated (1608) and rear balloon 1104 inflated to the point of substantially securing probe apparatus 1100 to inner circumference of lumen 1102 while advancement balloon 1108 is at least partially inflated (1604) deploying front balloon 1106 forward, in accordance with an exemplary embodiment of the invention. FIG. 11D shows probe apparatus 1100 having successfully navigated the curve in lumen 1102 with front balloon 1106 inflated substantially securing probe apparatus 110 to the inner circumference of lumen 1102. Rear balloon 1104 and/or advancement balloon 1108 are at least partially deflated (1610), causing an overall retraction of probe apparatus 1100 and bring rear balloon 1104 past the curve, in accordance with an exemplary embodiment of the invention. In an embodiment of the invention, at least one of advancement balloon 1108 and/or rear balloon 1104 rotate/twist as retraction occurs. Forward motion of probe apparatus 1100 after successful navigation of curve follows the movement cycle shown and described with respect to FIGS. 9A-9F, in an exemplary embodiment of the invention.

Figure 12A:
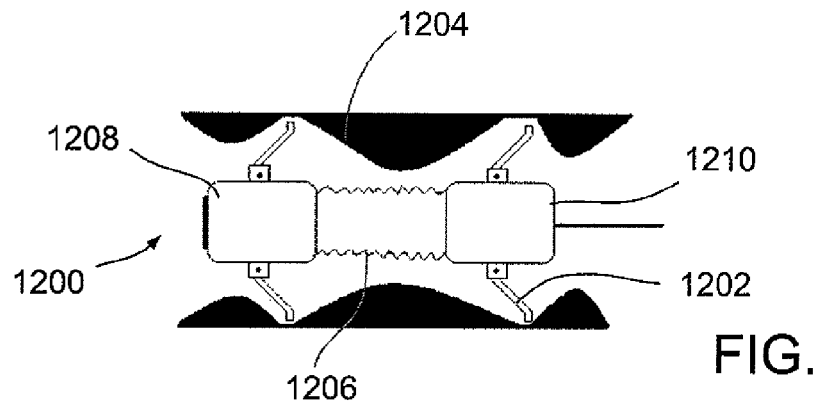
FIG. 12A is a cross-sectional view of an arm type probe apparatus in a retracted configuration, in accordance with an exemplary embodiment of the invention.

FIG. 12A shows probe apparatus 1200 with a linearly extendible and/or retractable element, such as an advancement balloon 1206, at least partially deflated with rear 1210 relatively close to front 1208 of probe apparatus 1200, in accordance with an exemplary embodiment of the invention. Optionally, the linearly extendible and/or retractable element is a piston, for example hydraulically or gas operated. While movement is provided by an advancement balloon 1206, direction of movement is determined by the bias applied to probe apparatus 1200 by a plurality of arm elements 1202.

In an embodiment of the invention, arm elements 1202 are used in lieu of the balloons of previously described balloon type probe apparatuses for substantially securing probe apparatus 1200 to the inner circumference of the lumen 1204. In addition to the securing functionality, arm elements 1202 are used to selectably bias probe apparatus 1200 for movement either forward or backward, in accordance with an exemplary embodiment of the invention. Securing is therefore only partial in that depending on which way arm elements 1202 bias probe apparatus 1200, movement is allowed in a first direction but not in a second, opposite direction, in accordance with an exemplary embodiment of the invention. Movement is caused by sequential inflation and/or deflation of an advancement balloon 1206 situated between a front 1208 and rear 1210 of probe apparatus 1200, in an embodiment of the invention.

Figure 12B:
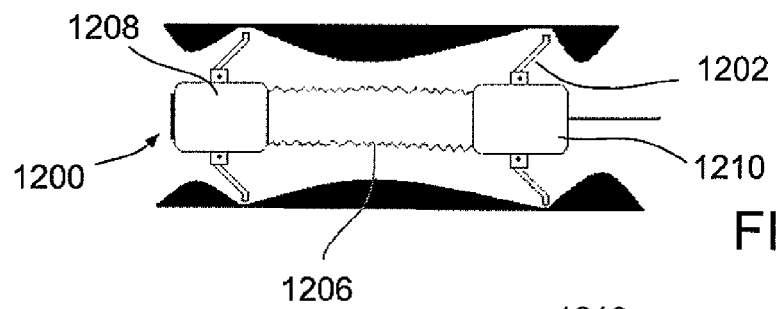
FIG. 12B is a cross-sectional view of an arm type probe apparatus in an extended configuration moving forward, in accordance with an exemplary embodiment of the invention.

FIG. 12B is a cross-sectional view of an arm type probe apparatus 1200 in an extended configuration moving forward, in accordance with an exemplary embodiment of the invention. It can be seen that probe apparatus 1200 moved forward by inflation of advancement balloon 1206 which pushed front 1208 forward. Forward motion of front 1208 was allowed by arm elements 1202 on front 1208, however rear 1210 was secured to lumen as backward motion of rear 1210 was prevented by the bias of the arm elements 1202, in accordance with an exemplary embodiment of the invention.

Figure 12C:
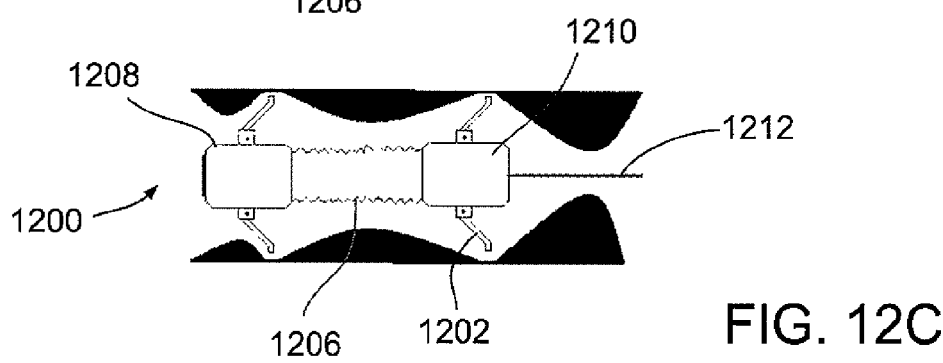
FIG. 12C is a cross-sectional view of an arm type probe apparatus retracting an advancement balloon towards the front, in accordance with an exemplary embodiment of the invention.

As shown in FIG. 12C, the movement cycle of probe apparatus 1200 is concluded by deflating advancement balloon 1206, in an embodiment of the invention. Front 1208 remains stationary as the bias of the arm elements 1202 prevents front 1208 from moving backwards while rear 1210 moves forward towards front 1208 being permitted to do so by the arm element 1202 bias toward forward motion, in an embodiment of the invention.

Figure 12D:
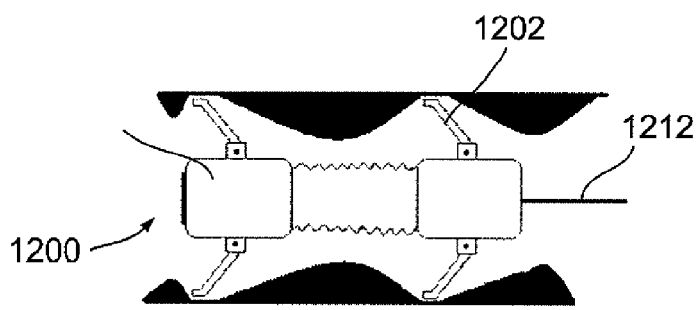
FIG. 12D is a cross-sectional view of an arm type probe apparatus in a retracted configuration moving backwards, in accordance with an exemplary embodiment of the invention.

In an embodiment of the invention, switching the bias of arm elements 1202 enables the probe apparatus 1200 to switch its direction of travel. Probe apparatus 1200 is adapted for switching arm element 1202 bias, for example by having arm extensions 1202 pivotable around their base where they attach to front 1208 and/or rear 1210. By pulling on a supply line 1212 (for supplying power, inflation material, etc. to a probe apparatus) in a proximal direction, the bias of arm elements 1202 is changed from forward movement to backward movement, as shown in FIG. 12D, in accordance with an exemplary embodiment of the invention.

Figure 12E:
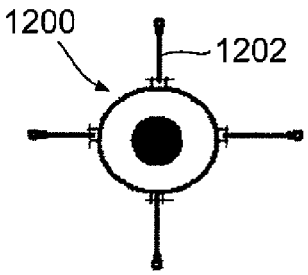
FIG. 12E is a front view of an arm type probe apparatus, in accordance with an exemplary embodiment of the invention.

FIG. 12E shows the front of probe apparatus 1200, in accordance with an exemplary embodiment of the invention. It should be noted that although 4 arm elements 202 are shown, any number of arm elements is used which provide a safe interface with the lumen wall and/or stable positioning of probe apparatus 1200 with respect to the lumen and/or adequate movement capability with the lumen.

In some embodiments of the invention, probe apparatus 1200 is adapted with an advancement balloon configuration similar to that of the advancement balloon depicted in FIGS. 1A-1H and FIGS. 4A-4B, wherein balloon 104 is provided with a sealing sleeve and no sliding gasket is necessary for the apparatus. In some embodiments of the invention, the advancement balloon of probe apparatus 1200 is of a configuration similar to that of the advancement balloon depicted in FIGS. 3A-3B and 5A-5B, wherein no sealing sleeve is provided to the probe apparatus and a sliding gasket is used to prevent leakage of inflation material from the apparatus.

Figure 13A:
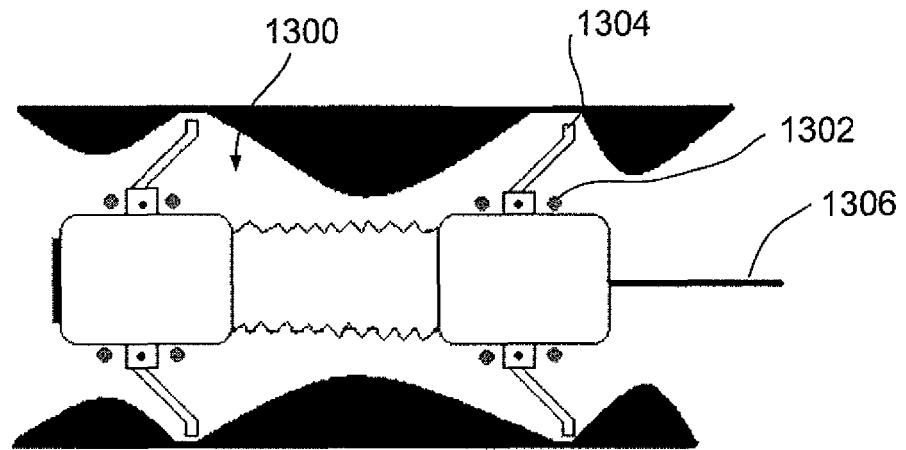
FIGS. 13A-B are side views of an arm type probe apparatus adapted with at least one balloon for switching arm direction, in accordance with an exemplary embodiment of the invention.
Figure 13B:
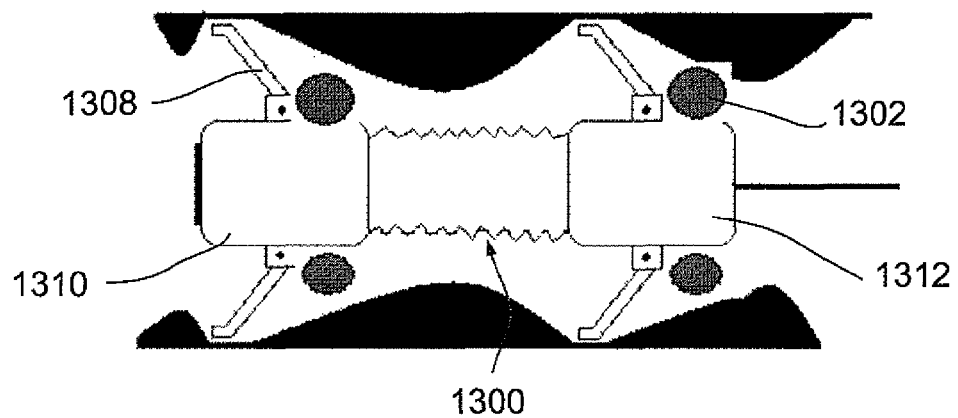

Referring to FIGS. 13A-B, side views of an arm type probe apparatus 1300 adapted with at least one balloon 1302 for switching arm element 1304 direction and/or arm element 1304 angle are shown, in accordance with an exemplary embodiment of the invention. Probe apparatus 1300 functions similarly to probe apparatus 1200 with the addition of the at least one balloon 1302, in an exemplary embodiment of the invention. In some embodiments of the invention, selective inflation of at least one balloon 1302 is used in combination with pulling on a supply line 1306 and/or a in a proximal direction to change the bias of arm elements 1304 from forward movement to backward movement. In an embodiment of the invention, supply line 1306 provides inflation material to the at least one balloon 1302 and/or provides an evacuation means for deflating the at least one balloon 1302, for example by applying vacuum suction to supply line 1306.

It should be noted that in some exemplary embodiments of the invention, switching the bias of an arm element 1304 is achieved without the assistance of pulling on supply line 1306. In some embodiments of the invention, a balloon is located on either side of arm element 1304, enabling switching from forward motion to backward motion and/or vice versa.

In an embodiment of the invention, selective inflation and/or deflation of balloon 1302 allows for setting the angle of incidence of arm element 1304 to probe apparatus 1300 and/or the lumen.

In FIG. 13A, probe apparatus 1300 is biased for forward movement and at least one balloon 1302 is at least partially deflated such that sufficient pressure to alter the bias of an arm element is not exerted on the arm element 1304 by the balloon 1302. FIG. 13B shows probe apparatus 1300 biased for backwards movement at least partially as a result of inflation of balloons 1302, 1308, in an embodiment of the invention. In some embodiments of the invention, balloons 1302, 1308 are toroidal in shape and are wrapped around front 1310 and/or rear 1312 of apparatus 1300 so that inflation of one of the balloons 1308, 1302 affects the arm elements attached to front 1310 and/or rear 1312, respectively. Alternatively and/or optionally, each arm element is provided with an independently inflatable/deflatable balloon.

FIGS. 14A-D are side views of various arm element configurations, in accordance with exemplary embodiments of the invention. In order to prevent lumen tissue perforation while changing bias direction of arm elements, the surface area of arm elements where they contact the lumen can be enhanced, in some exemplary embodiments of the invention. For example, FIG. 14A shows an arm element 1400 enhanced with a ball tip 1402. In an embodiment of the invention, ball tip 1402 is produced from a "soft" material (e.g. silicone, epdm rubber, sponge).

In an embodiment of the invention, an arm element 1420 is shown in FIG. 14B which is adapted to enhance the biasing feature of the arm type probe apparatuses. In an embodiment of the invention, arm element 1420 is provided with a v-shaped tip 1422 to provide better securing force while also being able to change bias direction from forward 1424 to backward 1426 (and/or vice versa) and/or allow for motion in the desired direction after bias switching.

In some exemplary embodiments of the invention, an arm element is adapted to reduce its overall length dimension to ease bias switching. For example, the arm element is provided with an extendible shape such that during bias switching, the arm element reduces overall length but when deployed in either forward or backward movement bias, the arm element attains the maximum length allowable by the lumen and/or the length of the arm element. In an embodiment of the invention depicted in FIG. 14C, an arm element 1442 is extendible and is provided with a compression spring 1444 which tends to extend, not shorten, the extending arm element 1442. As shown in FIG. 14D, arm element 1442 reduces overall length during bias switching using spring 1444 compression, reducing pressure exerted by arm element 1442 on the lumen wall 1446 during operation, in accordance with an exemplary embodiment of the invention.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A probe apparatus adapted for movement through a lumen, comprising:
    a linearly extendible and retractable element adapted for selective extension and retraction;
    a front balloon positioned forward of the linearly extendible and retractable element and adapted for selective inflation and deflation;
    a rear balloon positioned backward of the linearly extendible and retractable element and adapted for selective inflation and deflation; and,
    a twisting element adapted to twist at least one of the linearly extendible and retractable element, front balloon and rear balloon during extension and retraction of the linearly extendible and retractable element,
    wherein cyclic extension and retraction of the linearly extendible and retractable element in combination with selective inflation and deflation of the front and rear balloons provides movement to the apparatus.

2. A probe apparatus according to claim 1, wherein the linearly extendible and retractable element is a selectively inflatable and deflatable advancement balloon.

3. A probe apparatus according to claim 1, wherein the twisting device comprises a spring.

4. A probe apparatus according to claim 1, wherein the twisting device comprises at least one elastic band.

5. A probe apparatus according to claim 1, wherein the probe apparatus is adapted with an instrument channel for accommodating the insertion of at least one medical instrument.

6. A probe apparatus according to claim 5, wherein the instrument channel twists independently of the linearly extendible and retractable element, front balloon and rear balloon.

7. A probe apparatus according claim 1, wherein the probe apparatus is provided with at least one supply line.

8. A probe apparatus according to claim 7, wherein the supply line provides power to the probe apparatus.

9. A probe apparatus according to claim 7, wherein the supply line provides inflation material to the probe apparatus.

10. A probe apparatus according to claim 2, further comprising a sealing sleeve for insulating contents of the advancement balloon from an interior of the probe apparatus.

11. A probe apparatus according to claims 1, further comprising a sliding gasket adapted to prevent inflation material from leaking out of probe apparatus.

12. A probe apparatus according to claim 2, wherein a surface of at least one of the front balloon, rear balloon and the advancement balloon is textured to interface with an inner circumference of the lumen.

13. A probe apparatus according to claim 1, wherein at least one of the front balloon and rear balloon is comprised of a plurality of independently inflatable and deflatable balloons.

14. A probe apparatus according to claim 1, further comprising a jointed tip.

15. A probe apparatus according to claim 14, wherein the jointed tip is deflected by the inflation of at least one balloon.

16. A method of using a balloon type probe apparatus, comprising:
    inserting the probe apparatus in a lumen;
    inflating a rear balloon of the probe apparatus, substantially securing the probe apparatus in place in the lumen;
    at least partially extending a linearly extendible and retractable element of the probe apparatus to move a front balloon of the probe apparatus forward in the lumen;
    twisting at least one of the rear balloon, linearly extendible and retractable element and front balloon during the at least partially extending of the linearly extendible and retractable element;
    inflating the front balloon, substantially securing the probe apparatus in place in the lumen without regard for the rear balloon securing; and,
    deflating, at least partially, the rear balloon and retracting the linearly extendible and retractable element drawing the rear balloon closer to the front balloon.

17. A method according to claim 16, wherein at least one of a supply line or an instrument channel of the probe apparatus does not twist relative to the lumen when at least one of the rear balloon, linearly extendible and retractable element and front balloon twists.

18. A method according to claim 16, further comprising restarting the method at deflating the front balloon after re-inflating the rear balloon.

19. A method of navigating a curve in a lumen, comprising:
inserting the probe apparatus in a lumen;
inflating a rear balloon of the probe apparatus, substantially securing the probe apparatus in place in the lumen;
at least partially extending and twisting a linearly extendible and retractable element of the probe apparatus to move a front balloon of the probe apparatus forward and around the curve in the lumen;
inflating the front balloon, substantially securing the probe apparatus in place in the lumen without regard for the rear balloon securing; and,
deflating, at least partially, the rear balloon and retracting and twisting the linearly extendible and retractable element drawing the rear balloon closer to the front balloon and around the curve in the lumen.

* * * * *